United States Patent
Rasmussen et al.

(10) Patent No.: US 9,571,949 B2
(45) Date of Patent: Feb. 14, 2017

(54) APPARATUS FOR DETERMINING COCHLEAR DEAD REGION

(71) Applicants: OTICON A/S, Smørum (DK); BERNAFON AG, Berne (CH)

(72) Inventors: Karsten Bo Rasmussen, Smørum (DK); Barbara Simon, Berne (CH); Neil Hockley, Berne (CH); Christophe Lesimple, Berne (CH); Thomas Ulrich Christiansen, Smørum (DK); Monika Bertges Reber, Heitenried (CH)

(73) Assignees: OTICON A/S, Smorum (DK); BERNAFON AG, Berne (CH)

( * ) Notice: Subject to any disclaimer, the term of this patent is extended or adjusted under 35 U.S.C. 154(b) by 108 days.

(21) Appl. No.: 14/614,108

(22) Filed: Feb. 4, 2015

(65) Prior Publication Data

US 2015/0222999 A1 Aug. 6, 2015

(30) Foreign Application Priority Data

Feb. 5, 2014 (EP) .................................. 14153947

(51) Int. Cl.
*H04R 29/00* (2006.01)
*H04R 25/00* (2006.01)
(Continued)

(52) U.S. Cl.
CPC ............... *H04R 25/70* (2013.01); *A61B 5/123* (2013.01); *A61B 5/16* (2013.01); *A61B 5/7475* (2013.01);
(Continued)

(58) Field of Classification Search
CPC ............ H04R 2225/67; H04R 2225/43; H04R 2225/025; H04R 25/00; H04R 25/48; H04R 25/50; H04R 25/70; H04R 25/552; H04R 25/606; A61B 5/16; A61B 5/123

See application file for complete search history.

(56) References Cited

U.S. PATENT DOCUMENTS

| 8,233,651 | B1 * | 7/2012 | Haller ................ A61N 1/36032 381/318 |
| 8,768,478 | B1 * | 7/2014 | James ................ A61N 1/36032 607/57 |

(Continued)

FOREIGN PATENT DOCUMENTS

EP      0 661 905 A2     7/1995

OTHER PUBLICATIONS

Simpson et al., "Benefits of audibility for listeners with severe high-frequency hearing loss", Elsevier, Hearing Research, 2005, vol. 210, pp. 42-52.

*Primary Examiner* — Thang Tran
(74) *Attorney, Agent, or Firm* — Birch, Stewart, Kolasch & Birch, LLP

(57) ABSTRACT

An apparatus for determining cochlear dead region comprising a sound generation unit, an output transducer, and a control unit. The control unit causes the sound generation unit to provide a first electrical sound signal representing a first frequency band adjacent to a frequency region of interest, with a first bandwidth, a first sound pressure level and a first subsequent electrical sound signal representing a first subsequent frequency band comprising the frequency region of interest with a first subsequent bandwidth, a first subsequent sound pressure level, and a first subsequent time delay to the first electrical sound signal. In response, the output transducer generates a first output sound and a first subsequent output sound with the first subsequent time delay. A user compares the first output and first subsequent output sounds and decides, whether he hears a difference (Continued)

between the two sounds and gives a positive or negative decision input.

20 Claims, 7 Drawing Sheets

(51) Int. Cl.
    *A61B 5/16*     (2006.01)
    *A61B 5/12*     (2006.01)
    *A61B 5/00*     (2006.01)

(52) U.S. Cl.
    CPC ......... *H04R 25/606* (2013.01); *H04R 2225/43* (2013.01)

(56) References Cited

U.S. PATENT DOCUMENTS

| | | | |
|---|---|---|---|
| 9,072,468 B2* | 7/2015 | Buchman | A61B 5/121 |
| 2006/0161227 A1* | 7/2006 | Walsh | A61N 5/0603 |
| | | | 607/88 |
| 2007/0293785 A1* | 12/2007 | Litvak | A61N 1/36032 |
| | | | 600/559 |
| 2008/0228101 A1* | 9/2008 | Allen | A61B 5/411 |
| | | | 600/559 |
| 2008/0249589 A1* | 10/2008 | Cornejo Cruz | A61B 5/04845 |
| | | | 607/57 |
| 2009/0024185 A1 | 1/2009 | Kulkarni et al. | |
| 2010/0202625 A1 | 8/2010 | Boretzki et al. | |
| 2012/0265093 A1* | 10/2012 | Allen | A61B 5/411 |
| | | | 600/559 |
| 2012/0300964 A1* | 11/2012 | Ku | A61B 5/04845 |
| | | | 381/321 |
| 2013/0023964 A1* | 1/2013 | Stafford | A61N 5/0622 |
| | | | 607/88 |
| 2014/0119583 A1* | 5/2014 | Valentine | H04R 25/70 |
| | | | 381/316 |
| 2014/0309712 A1* | 10/2014 | Masaki | A61N 1/36032 |
| | | | 607/57 |
| 2015/0265837 A1* | 9/2015 | Kulkarni | H04R 25/407 |
| | | | 381/313 |

* cited by examiner

APPARATUS FOR DETERMINING COCHLEAR DEAD REGION

FIELD

The disclosure relates to an apparatus for determining cochlear dead region. In particular, the disclosure relates to a hearing aid device comprising a sound generation unit, an output transducer and a control unit and a method for determining cochlear dead regions.

BACKGROUND OF THE RELATED ART

Hearing or auditory perception is the process of perceiving sounds by detecting mechanical vibrations with a sound vibration input. A human ear has three main components, an outer ear, a middle ear and an inner ear. Each part of the ear serves a specific purpose in the task of detecting and interpreting sound. The outer ear serves to collect and channel sound to the middle ear. The middle ear serves to transform the energy of a sound wave into the internal vibrations of the bone structure of the middle ear and ultimately transform these vibrations into a compressional wave in the inner ear. The inner ear serves to transform the energy of a compressional wave within the inner ear fluid into nerve impulses that can be transmitted to the brain.

The inner ear is the innermost part of the ear, which begins behind an oval window. The oval window, which serves as an intersection between middle ear and inner ear, is a membrane covered opening which receives mechanical vibrations from stapes of the middle ear. The inner ear comprises a bony labyrinth, which is a hollow cavity located in a temporal bone of the skull with two functional parts, a cochlea, and a vestibular system formed by semicircular canals and a vestibule. The bony labyrinth comprises a membranous labyrinth which is in certain locations fixed to a wall of the bony labyrinth and partly separated from the bony labyrinth by the perilymph. The membranous labyrinth contains a liquid, called endolymph. The perilymph is rich in sodium ions and the endolymph is rich in potassium ions, which produces an ionic electrical potential between the perilymph and the endolymph. The unique ionic compositions of the perilymph and the endolymph are adapted for regulating electrochemical impulses of hair cells. Hair cells are cylindrical or flask-shaped cells with a bundle of sensory hairs at their apical end, also called stereocilia. Inner hair cells are arranged on an inner wall and outer hair cells are arranged on an outer wall in specialized areas of the membranous labyrinth. The hair cells are connected to nerve fibres of a vestibulocochlear nerve comprising a vestibular nerve and a cochlear nerve and work as receptor cells of vibratory stimuli of the perilymph and endolymph. The hair cells in the vestibular system serve to sense spatial orientation information and transmit them to a brain via the vestibular nerve generating a sense of balance. One of the specialized areas of the membranous labyrinth is a spiral organ called organ of Corti, which comprises hair cells serving for auditory perception.

The organ of Corti is arranged in the cochlea. The cochlea is a spiral-shaped perilymph filled cavity in the bony labyrinth in contact with the oval window via the vestibule. The spiral of the cochlea typically has 2.5 to 2.75 turns around its axis for a human. The structure of the cochlea includes a scala vestibuli, a scala tympani, a scala media, and a helicotrema. The perilymph filled scala vestibuli joins the perilymph filled scala tympani at the apex of the cochlea, also called helicotrema. On the other end the scala vestibuli is connected to the oval window and the scala tympani is connected to a round window. The round window vibrates with opposite phase to the oval window, e.g. the round window moves out when the stirrup pushes in the oval window and allows movement of the liquid inside of the cochlea. The scala media is located between the scala tympani and the scala vestibuli, separated from the scala tympani by a basilar membrane, and separated from the scala vestibuli by a Reissner's membrane. The scala media contains endolymph. The Reissner's membrane functions as a diffusion barrier for nutrients between perilymph and endolymph. The basilar membrane determines the mechanical vibration propagation properties and is the base of the hair cells containing the steriocilia. The cochlea serves for converting mechanical vibrations received by the ear drum into electrochemical nerve impulses which are then passed to the brain via the cochlear nerve, also called acoustic nerve.

Mechanical vibration stimuli transmitted by the perilymph run through the cochlea and excite the membrane of the membranous labyrinth and the hair cells. Each frequency of the mechanical vibrations received has a specific place of resonance along the basilar membrane of the membranous labyrinth in the cochlea. The movement of the basilar membrane and the mechanical vibrations in the perilymph lead to movement of the stereocilia on the hair cells. The outer hair cells oscillate in cell length with a frequency of an incoming vibration, which serves to amplify incoming mechanical vibrations, called cochlear amplifier. The inner hair cell works as a mechanoreceptor, which produces an electrical signal in response to displacement of the stereocilia of the inner hair cell. The electrical signal originates from a flow of ionic currents across the membrane of the membranous labyrinth through ion channels. The stereocilia of the inner hair cells have a depolarization and a repolarization movement direction. The movement of the stereocilia in depolarization direction leads to increased membrane conductance, allowing more positively charged ions, i.e. potassium and calcium, to pass the membrane and to enter the inner hair cell. Movement in the repolarization direction lowers ionic current. Depolarization of the inner hair cells occurs due to influx of positive ions resulting in a receptor potential, which opens voltage-dependent calcium channels (VDCC). Calcium ions can enter the cell through the voltage-dependent calcium channels (VDCC) and trigger the release of neuro-transmitters which connect to receptors of the fibres, also called axons, of the cochlear nerve connected to the hair cells resulting in increased firing, i.e. emission of electrochemical nerve impulses. Repolarization of the hair cells occurs due to low concentration of positive ions in the perilymph in the scala tympani, which leads to an electrochemical gradient and a flow of positive ions through ion channels to the perilymph. The electrochemical nerve impulses are transmitted to the brain via the cochlear nerve. The brain processes the nerve impulses received by all hair cells and the spatial-temporal pattern of nerve impulses resulting from the firing of different hair cells in auditory perception.

Healthy human ears are able to hear sounds in a frequency range of 0.012 kHz to 20 kHz and have a sensitivity peak in a range between 1 kHz to 5 kHz. The human ear can resolve frequency differences down to 3.6 Hz, allowing humans to differentiate between two sounds with a difference as small as 3.6 Hz. With age the hearing deteriorates, called Presbycusis or age-related hearing loss, which leads to a lower audible hearing frequency range. Most adults are unable to hear high frequencies above 16 kHz. The cause of age-related hearing loss is typically a sensorineural hearing loss.

The hearing can be considered impaired, if one or more of the functions of one or both ears of a human are impaired. A hearing impairment can be classified as sensorineural hearing loss, conductive hearing loss or a combination of the two called mixed hearing loss.

The most common kind of hearing impairment is the sensorineural hearing loss, which results from impairment of the vestibulocochlear nerve, the inner ear, and/or central processing centers of the brain. A majority of sensorineural hearing loss is caused by dysfunction of the hair cells of the organ of Corti in the cochlea leading to decreased hearing sensitivity. The hair cells can be dysfunctional at birth or damaged, e.g., due to noise trauma, infection, long time noise exposure, or genetic predisposition. Often the outer hair cells, which are particularly sensitive to damage from exposure to trauma from overly-loud sounds or ototoxic drugs, are damaged and the amplification effect is lost.

Cochlear hearing loss which is a representative phenomenon of hearing impairment is related to damage to the hair cells of the cochlea, and this damage causes hearing loss in the following two forms.

A first form is damage to the outer hair cells, which is the cause of most sensorineural hearing loss. Due thereto, the active mechanism of the cochlea is damaged, so that the motion of a basilar membrane decreases compared to that of a normal state, with the result that frequency selectivity decreases. A second form is damage of inner hair cells. This may result in a decrease in the efficiency of signals transferred to a primary auditory cortex. In particular, speech recognition ability is greatly decreases, and the ability to discriminate signals from noise is further deteriorated in the presence of noise.

A region in which the inner hair cells are substantially damaged and in some cases completely lost and do not perform their own functions is called a cochlear dead region (DR). The cochlear dead region exhibits characteristics where the inner hair cells and nerves of the inside thereof do not induce nervous activities in response to stimuli falling within the range of relevant characteristic frequencies (CFs), and then relevant acoustic stimulus information is not transferred to a primary auditory cortex.

Some of the hearing impairments can be treated surgically. A major part of humans with a hearing impairment, however, has to rely on devices which improve hearing, so called hearing aid devices. Hearing aid devices are used to stimulate the hearing of a user, e.g., by sound generated by a speaker, by bone conducted vibrations generated by a vibrator of a bone anchored hearing aid, or by electric stimulation impulses generated by electrodes of a cochlear implant. Hearing aids can be worn on one ear, i.e. monaurally, or on both ears, i.e. binaurally. Binaural hearing aid devices comprise two hearing aids, one for a left ear and one for a right ear of the user. The binaural hearing aids can exchange information with each other wirelessly and allow spatial hearing.

Hearing aids typically comprise a microphone, an output transducer, e.g. speaker or vibrator, electric circuitry, and a power source, e.g., a battery. The microphone receives a sound from the environment and generates an electrical sound signal representing the sound. The electrical sound signal is processed, e.g., frequency selectively amplified, noise reduced, adjusted to a listening environment, and/or frequency transposed or the like, by the electric circuitry and a processed sound is generated by the output transducer to stimulate the hearing of the user. Instead of an output transducer the cochlear implant typically comprises an array of electrodes, which are arranged in the cochlea to stimulate the cochlear nerve fibres with electric stimulation impulses. In order to improve the hearing experience of the user a spectral filterbank can be included in the electric circuitry, which, e.g., analyses different frequency bands or processes electrical sound signals in different frequency bands individually and allows improving the signal-to-noise ratio. Spectral filterbanks are typically running online in any hearing aid today.

Typically the microphones of the hearing aid device used to receive the incoming sound are omnidirectional, meaning that they do not differentiate between the directions of the incoming sound. In order to improve the hearing of the user, a beamformer can be included in the electric circuitry. The beamformer improves the spatial hearing by suppressing sound from other directions than a direction defined by beamformer parameters, i.e. a look vector. In this way the signal-to-noise ratio can be increased, as mainly sound from a sound source, e.g., in front of the user is received. Typically a beamformer divides the space in two sub-spaces, one from which sound is received and the rest, where sound is suppressed, which results in spatial hearing.

For certain acoustical environments, a microphone to record direct sound can be insufficient to generate a suitable hearing experience for the hearing aid device user, e.g., in a highly reverberant room like a church, a lecture hall, a concert hall or the like. Therefore hearing aid devices can include a second input for sound information, e.g., a telecoil or a wireless data receiver, such as a Bluetooth receiver or an infrared receiver, or the like. When using telecoil or other wireless technology an undistorted target sound, e.g., a priest's voice in a church, a lecturer's voice in a lecture hall, or the like is available directly in the hearing aid by wireless sound transmission.

One way to characterize hearing aid devices is by the way they are fitted to an ear of the user. Conventional hearing aids include for example ITE (In-The-Ear), ITC (In-The-Canal), CIC (Completely-In-the-Canal) and BTE (Behind-The-Ear) hearing aids. The components of the ITE hearing aids are mainly located in an ear, while ITC and CIC hearing aid components are located in an ear canal. BTE hearing aids typically comprise a Behind-The-Ear unit, which is generally mounted behind or on an ear of the user and which is connected to an air filled tube or a lead that has a distal end that can be fitted in an ear canal of the user. Sound generated by a speaker can be transmitted through the air filled tube to an ear drum of the user's ear canal or an electrical sound signal can be transmitted to an output transducer arranged in the ear canal via the lead.

Nearly all hearing aids have at least one insertion part, which is adapted to be inserted into an ear canal of the user to guide the sound to the ear drum. Inserting the insertion part of a hearing aid device into an ear canal that transmits device generated sound into the ear canal can lead to various acoustic effects, e.g., a comb filter effect, sound oscillations or occlusion. Simultaneous occurrence of device generated and natural sound in an ear canal of the user creates the comb filter effect, as the natural and device generated sounds reach the ear drum with a time delay. Sound oscillations generally occur only for hearing aid devices including a microphone, with the sound oscillations being generated through sound reflections off the ear canal to the microphone of the hearing aid device. A common way to suppress the aforementioned acoustic effects is to close the ear canal, which effectively prevents natural sound to reach the ear drum and device generated sound to leave the ear canal. Closing the ear canal, however, leads to the occlusion effect, which corresponds to an amplification of a user's own voice when the ear canal is closed, as bone-conducted sound vibrations cannot escape through the ear canal and reverberate off the insertion part of the hearing aid device. To reduce the occlusion effect the insertion part of the hearing aid device can be inserted deeper into the ear canal to adhere to the bony portion of the ear canal and to seal the ear canal.

Hearing aid devices can be further improved, when the hearing impairment of the user is exactly known, e.g., by allowing an adjustment of hearing aid parameters to the hearing impairment of the user. Knowing the frequency range, for which a user has a reduced hearing ability allows for example to shift frequencies or amplify certain frequency ranges to allow for a better hearing experience of the user.

During processing of incoming sound in a hearing aid the amplification of frequencies in the frequency range corresponding to dead regions of the user is typically not beneficial and can impair speech intelligibility.

In conventional hearing care the cochlear dead region phenomenon is largely ignored due to the difficulty in establishing the existence and frequency region of the cochlear dead regions.

In B. C. Moore, M. Huss, D. A. Vickers, B. R. Glasberg, and J. I. Alcántara, "A Test for the Diagnosis of Dead Regions in the Cochlea" British Journal of Audiology, 34, 205-224 (2000) a method using a threshold equalizing noise (TEN) test to determine cochlear dead regions is presented. The TEN test stimulates the hearing of a user using a so called "threshold equalizing noise", which is spectrally shaped so that, for normally hearing users, it would give equal masked threshold for pure tone signals over all frequencies within a range of 0.25 kHz to 10 kHz. A level of the threshold equalizing noise is specified as a level in a one-ERB, equivalent rectangular bandwidth, (132 Hz) wide band centred at 1000 Hz. A pure tone is used with the threshold equalizing noise to stimulate the hearing of a user. The threshold equalizing noise reduces the off-frequency listening of the pure tone and therefore allows testing for cochlear dead regions. A frequency region with living inner hair cells leads to a detection of a signal with characteristic frequencies close to the frequency region and the threshold in the TEN is close to that for normal-hearing users. A dead region leads to a detection of characteristic frequencies different from that of the signal frequency and the threshold in the TEN is higher than normal.

WO 2012/081769 A1 presents an apparatus and a method for detecting a cochlear dead region. The apparatus comprises a control unit with a stimulus generation unit and an Acoustic Change Complex (ACC) measurement unit. The stimulus generation unit is configured to generate stimuli, which are provided to a user via a headphone and the Acoustic Change Complex measurement unit is configured to measure Acoustic Change Complexes depending on the stimuli. The Acoustic Change Complex is similar to a P1-N1-P2-complex and represents a cortical response due to change in the acoustic features of the stimuli. The P1-N1-P2-complex is a portion of cortical auditory evoked potential, which is a prior art test method to determine the degree of hearing of a user.

There exists a need for reliably identifying the cochlear dead region, and preferably offering schemes that allow for accounting for the determined dead regions in order to enhance hearing perception for a hearing impaired.

SUMMARY

According to an embodiment, an apparatus for determining cochlear dead region is disclosed. In an embodiment, the apparatus is a hearing aid device. Using the hearing aid allows for in situ determination of the cochlear dead region. The disclosure is described primarily in relation to the hearing aid device for in situ determination of the dead region. The same output transducer of the hearing aid device is used for the cochlear dead region determination, allowing for in situ determination of cochlear dead regions. It is understandable, however that the description is applicable for the apparatus that include similar components for providing same functionality as those included in the hearing aid device.

The apparatus (in another embodiment, a hearing aid device) comprises a sound generation unit, an output transducer, and a control unit. In case of the apparatus, such output transducer may include a headphone or other device providing similar functionality. The output transducer in case of the hearing device may include speaker of the hearing aid or other devices listed later in the description. The sound generation unit is configured to provide an electrical sound signal. The output transducer is configured to generate an output sound corresponding to the electrical sound signal. The control unit is configured to select a frequency region of interest. The region of interest may typically start from 1000 Hz but other starting frequency points are also feasible. Further the control unit is configured to cause the sound generation unit to provide a first electrical sound signal representing a first predetermined frequency band that is adjacent to the frequency region of interest. In an embodiment, the first predetermined frequency band does not comprise a frequency of the frequency region of interest.

The first electrical sound signal has a first predetermined bandwidth and a first predetermined sound pressure level. The control unit is further configured to select a first subsequent electrical sound signal representing a first subsequent predetermined frequency band comprising the frequency region of interest. The first subsequent electrical sound signal has a first subsequent bandwidth, a first subsequent predetermined sound pressure level, and a first subsequent predetermined time delay to the first electrical sound signal. The first subsequent predetermined frequency band comprises the first predetermined frequency band and the first subsequent bandwidth is wider than the first predetermined bandwidth. The output transducer is configured to generate a first output sound corresponding to the first electrical sound signal and a first subsequent output sound corresponding to the first subsequent electrical sound signal with the first subsequent predetermined time delay to the first electrical sound signal.

A cochlear dead region is detected, if a user does not hear any difference between the first output sound and the first subsequent output sound generated by the output transducer. In this scenario of inability of the user to hear any difference, the cochlear dead region corresponds to the frequency band that corresponds to the difference between a) the frequency band of the first electrical sound signal, and b) the frequency band of the first subsequent electrical sound signal. If a user hears a difference between the two output sounds at least a part of the frequency region of interest is activated by the stimulation with the first subsequent output sound. To determine if a smaller cochlear dead region is present, the subsequent bandwidth may be decreased. It is also possible to change the bandwidth or region of interest by shifting the frequency bands of the electrical sound signals and varying their bandwidths.

One aspect of the disclosure is that a cochlear dead region can be determined faster than in the prior art, e.g., determination by psychoacoustic tuning curves or threshold equalized noise (TEN) test. An aspect of an embodiment of the disclosure, where the apparatus is the hearing aid device, the same output transducer of the hearing aid device is used for the cochlear dead region determination and for hearing improvement by emitting amplified sound, which allows in situ determination of cochlear dead regions. Further the user's ear acoustics are taken into account, no additional equipment is needed and the danger of collapsing canals occurring frequently in cochlear dead region determination over headphones is diminished. The output transducer is new and in spec, as the output transducer comes fresh off the production line. The possibility of in situ audiometry can for example potentially reduce over amplification in high frequencies caused by phantom air bone gaps and higher thresholds that result due to collapsing canals.

In a preferred embodiment, the apparatus (in another embodiment, hearing aid device) comprises a user interface configured to receive positive decision inputs and negative decision inputs by a user using the user interface. Preferably, the user interface is configured to provide the positive decision inputs and negative decision inputs to the control unit. The control unit is preferably configured to provide an n-counter, which is an integer counter initialized with n=1. The initialization of counter leads to comparison between two output sounds. Preferably, the control unit is further configured to cause the sound generation unit to increase the n-counter by 1 whenever the control unit receives a positive decision. The positive decision input corresponds to the ability of a user to hear a sound at the current sound pressure level and leads to re-initialization of the comparison between two output sounds with adjusted parameters. Further, the control unit is preferably configured to cause the sound generation unit, each time a positive decision input is received by the control unit, to provide an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal. The electrical sound signals provided by the sound generation unit are preferably narrow band noise signals, e.g., derived from 1/f pink noise or similar narrow band noise signals. The sound pressure level is preferably above an overall hearing threshold of a user using the hearing aid device. In the preferred embodiment the n-th subsequent predetermined frequency band comprises the first predetermined frequency band and the n-th subsequent predetermined bandwidth is narrower than the (n−1)-th subsequent predetermined bandwidth. The control unit is preferably configured, each time a positive decision input is received by the control unit, to cause the output transducer to generate a first output sound corresponding to the first electrical sound signal and an n-th subsequent output sound corresponding to the n-th subsequent electrical sound signal with the n-th subsequent predetermined time delay to the first electrical sound signal. If a negative decision input is received by the control unit, the control unit is preferably configured to detect the cochlear dead region in the frequency band corresponding to the difference between the frequency bands of the first electrical sound signal and the n-th subsequent electrical sound signal.

In an embodiment, the apparatus (in another embodiment, the hearing aid device) comprises a memory configured to store data, e.g., audiogram data, modes of operation, algorithms, electrical signals, audiograms or other data.

In one embodiment, the control unit is configured to execute various modes of operation, e.g., hearing aid mode, audiogram generation mode, cochlear determination mode, silent mode, or other modes of operation.

In one embodiment of an audiogram generation mode, the control unit is configured to cause the sound generation unit to provide an electrical sound signal representing a predetermined frequency with a predetermined sound pressure level. The electrical sound signal can for example be a sine wave with a predetermined frequency and a sound pressure level corresponding to the amplitude of the sine wave. Preferably, the output transducer operating in the audiogram generation mode is configured to generate an output sound corresponding to the electrical sound signal. The output sound is preferably a pure tone. The control unit operating in the audiogram generation mode is preferably further configured to increase the predetermined sound pressure level over time until a positive decision input for the predetermined frequency is received by the user interface or a maximal threshold sound pressure level for the predetermined frequency is reached. The increase can be after constant time steps or adaptively. Preferably the predetermined sound pressure level is increased after a predetermined duration. The memory operating in the audiogram generation mode is preferably configured to store the sound pressure level for the predetermined frequency in audiogram data each time a positive decision input is received for a predetermined frequency by the user interface or the maximal threshold sound pressure level for a predetermined frequency is reached. Further, the control unit operating in the audiogram generation mode is preferably configured to shift the predetermined frequency each time a positive decision input is received for a predetermined frequency or the maximal threshold sound pressure level for a predetermined frequency is reached. The shift can for example be by increasing, decreasing or changing the predetermined frequency, e.g., increasing/decreasing by fixed or adaptive steps, or changing to predetermined values or random values. The step size can for example be smaller in a region between 2 kHz to 4 kHz. The region of 2 to 4 kHz is generally interesting as a region of interest as steep descents of an audiogram are expected in these regions for users that are hearing-impaired. Preferably, the control unit is further configured to perform the audiogram generation mode for a predetermined frequency range and to generate an audiogram comprising user-specific sound pressure levels in dependence of frequencies using the audiogram data. The audiogram can be provided to the memory and stored in the memory. Alternatively the audiogram data can form an audiogram.

In one embodiment of the audiogram generation mode the audiogram generation mode is controlled by a time limit that stops the audiogram generation mode as soon as the time limit is reached. In one embodiment it is also possible to omit certain sound pressure levels and/or predetermined frequencies when increasing the sound pressure level and/or shifting the predetermined frequency, for example if knowledge exists that some common sound pressure levels and/or frequencies lead to output sounds that cannot be heard by a peer group or an average human. Also in one embodiment the audiogram generation mode can be performed by decreasing the sound pressure level until a user does not hear a sound anymore. This however is not preferable, as loud sounds can hurt hair cells of the user or destroy the hair cells causing cochlear dead regions. In one embodiment of the audiogram generation mode, the audiogram generation mode is performed continuously until a user manually stops the audiogram generation mode.

In one embodiment, the control unit is configured to obtain an audiogram and to select a frequency region of interest in dependence of the audiogram. The audiogram can be either the audiogram generated by the audiogram generation mode or an audiogram received from an external device, the memory, or another source for audiograms. Preferably, the control unit is configured to identify a descent frequency region by determining a descent in the audiogram and to select the identified descent frequency region as frequency region of interest. The control unit can also be configured to use a TEN test, a psychoacoustic tuning curve, or a previous region of interest saved in the memory as indication for selecting the frequency region of interest.

The hearing aid device is preferably configured to be worn on or at an ear of a user. In one embodiment, the hearing aid device is a behind-the-ear (BTE) hearing aid. In another embodiment, the hearing aid device can also be a completely-in-the-channel (CIC) hearing aid, in-the-canal (ITC) hearing aid or in-the-ear (ITE) hearing aid. The hearing aid device can also be a binaural hearing aid device with one hearing aid worn at or on each of the ears of a user.

In a preferred embodiment, the first predetermined bandwidth of the first electrical sound signal is between 300 Hz and 2 kHz, such as between 500 Hz and 1500 Hz. Also the subsequent bandwidth of the subsequent sound signals can be between 300 Hz and 2 kHz, such as between 500 Hz and 1500 Hz. Preferably, the bandwidth of the n-th subsequent electrical sound signals is wider than the bandwidth of the first electrical sound signal.

Preferably, the first output sound generated from the first electrical sound signal by the output transducer has a predetermined duration. The predetermined time delay between the first electrical sound signal and an n-th subsequent electrical sound signal has preferably a duration corresponding to the predetermined duration, so that the n-th subsequent electrical sound signal is provided to the output transducer the moment the emission of the first electrical sound signal is finished. This means a first output sound is emitted for a predetermined duration and an n-th subsequent output sound is emitted immediately after the emission of the first output sound is finished. There can also be a time delay creating a small period of silence between the two emissions of the first output sound and the n-th subsequent output sound. The predetermined duration of the first output sound is preferably equal to or below 5 s, such as equal to or below 2 s, such as equal to or below 1 s or a suitably selected predetermined duration. It is also possible that n-th subsequent output sounds have durations equal to the duration of the first output sound or another duration. Preferably, the duration of the first output sound and the n-th subsequent output sound are equal.

In a preferred embodiment, the generation unit is configured to provide electrical sound signals that correspond to 1/f-pink noise with a predetermined frequency band, a predetermined frequency bandwidth, and a predetermined sound pressure level. Preferably, the electrical sound signals generate an output sound with a predetermined duration when processed in an output transducer. The frequency band can also be defined by a centre frequency and the bandwidth.

In one embodiment, each of the first predetermined sound pressure level and the n-th subsequent predetermined sound pressure level is equal to or above 70 dB SPL, such as equal to or above 80 dB SPL, such as equal to or above 90 dB SPL, such as equal to or above 100 dB SPL. Preferably, the sound pressure level is above an overall hearing threshold of the user. The sound pressure level of the first and the n-th subsequent sound pressure level can be different or equal. Preferably, they are equal.

In an embodiment, the apparatus is a hearing aid device. The hearing aid device preferably comprises at least a microphone and electric circuitry. Preferably, the microphone is configured to receive environment sound and to generate electrical environment sound signals. The electric circuitry is preferably configured to process electrical environment sound signals and to generate output sound signals. The output transducer of the hearing aid device is preferably configured to generate output sounds corresponding to the output sound signals received from the electric circuitry. The hearing aid can further comprise a telecoil or any other wireless sound signal input. The telecoil is preferably configured to receive wireless sound signals and to generate electrical wireless sound signals which can be processed by the electric circuitry into an output sound signal.

The disclosure also concerns a method for determining cochlear dead regions of a user. The method for determining cochlear dead regions can be performed using the apparatus and in another embodiment using the hearing aid device according to the disclosure. The method preferably comprises the step of obtaining an audiogram. The method further preferably comprises a step of selecting a frequency region of interest in the audiogram. The frequency region of interest is preferably derived from an audiogram by determining a descent in the audiogram, which gives an indication for a frequency region of interest. The method can also comprise a step of randomly selecting a frequency region of interest or another method to determine a frequency region of interest than to analyse the audiogram, e.g., from a psychoacoustic tuning curve or previous TEN test. The method comprises a step of providing a first electrical sound signal representing a first predetermined frequency band adjacent to the frequency region of interest which does not comprise a frequency of the frequency region of interest, with a first predetermined bandwidth and a first predetermined sound pressure level. The method further comprises a step of providing a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal. The first subsequent predetermined frequency band preferably comprises the first predetermined frequency band and the first subsequent predetermined bandwidth is wider than the first predetermined bandwidth. The method further comprises a step of emitting a first output sound corresponding to the first electrical sound signal for a first predetermined duration. Further the method comprises a step of emitting a first subsequent output sound corresponding to the first subsequent electrical sound signal with the first subsequent predetermined time delay to the first electrical sound signal for a first subsequent predetermined duration. The method can comprise a step of providing an n-counter with n=1. The method further comprises a step of receiving a positive decision input or a negative decision input in a predetermined time limit. The method can comprise a step of increasing the n-counter by 1, for each time a positive decision input is received within the predetermined time limit. The n-counter preferably is typically only increased by 1 for each predetermined time limit, meaning that receiving a positive decision input sets the predetermined time limit to its limit value and then resets the limit value for subsequent output sound signal. The method can further comprise a step of providing an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, for each time a positive decision input is received within the predetermined time limit. The n-th subsequent predetermined frequency band comprises the first predetermined frequency band. The n-th subsequent predetermined bandwidth is also narrower than the (n−1)-th subsequent predetermined bandwidth. The method can further comprise a step of emitting the first output sound corresponding to the first electrical sound signal for the first predetermined duration and emitting the n-th subsequent output sound corresponding to the n-th subsequent electrical sound signal with the n-th subsequent predetermined time delay to the first electrical sound signal for an n-th predetermined duration, for each time a positive decision input is received within the predetermined time limit. The method further comprises a step of detecting, if a negative decision input is received, a cochlear dead region in the frequency band corresponding to the difference between the frequency bands of the first electrical sound signal and the n-th subsequent electrical sound signal. The predetermined time limit for receiving a decision input can be adaptive, for example it can change with the duration of the n-th predetermined duration. It is also possible that the first predetermined duration can be adaptive, for example also changing with the duration of an n-th predetermined duration.

The cochlear dead region determination can also be performed by a cochlear dead region determination unit. The cochlear dead region determination method can also be an algorithm or a mode of operation that can be executed on the control unit or a processing unit.

In a preferred embodiment of the method, the method further performs the following initial steps for a predetermined frequency range to generate an audiogram prior to performing the first step of the method of obtaining an audiogram. The audiogram generated by the following steps can be used by the method to determine a frequency region of interest. The method to generate an audiogram comprises a step of providing an electrical sound signal representing a predetermined frequency with a predetermined sound pressure level. The electrical sound signal is preferably a sine wave with the amplitude of the sine wave corresponding to the sound pressure level and the frequency of the sine wave being the predetermined frequency. Further the method comprises a step of emitting an output sound corresponding to the electrical sound signal. The output sound is preferably a pure tone generated for example from the sine wave. The method comprises a step of increasing the predetermined sound pressure level over time until a positive decision input for the electrical sound signal representing the predetermined frequency is received or a maximal threshold sound pressure level for the electrical sound signal representing the predetermined frequency is reached. The positive decision input corresponds to the ability of a user to hear a sound at the current sound pressure level. When the user is only able to hear a sound at a high sound pressure level, it can be an indication that a part of the hair cells present in that frequency region is impaired. The method can comprise a step of storing the sound pressure level for the predetermined frequency in audiogram data each time a positive decision input is received for an electrical sound signal representing a predetermined frequency or the maximal threshold sound pressure level for an electrical sound signal representing a predetermined frequency is reached. This stores a sound pressure level threshold that allowed hearing for a user with a frequency as audiogram data. The audiogram data can be used to generate an audiogram or corresponds to an audiogram when some frequencies are plotted with the data points of the sound pressure level thresholds determined by the method. The method further comprises a step of shifting the predetermined frequency each time a positive decision input is received for an electrical sound signal representing a predetermined frequency or the maximal threshold sound pressure level for an electrical sound signal representing a predetermined frequency is reached. The shifting can correspond to increasing, decreasing, or changing the value of the frequency. The shifting can occur predetermined, e.g., by increasing/decreasing by certain fixed or adaptive step sizes, changing to predetermined values, or randomly. The method can further comprise a step of generating an audiogram comprising user-specific sound pressure levels in dependence of frequencies using the audiogram data, if a predetermined number of frequencies has been stored as audiogram data. The audiogram can also be initiated manually by a user using the user interface or by the control unit via a command from an external device received by a receiver unit of the hearing aid. The audiogram generation can also be performed when the whole predetermined frequency range is covered. Alternatively, there can also be predetermined values in the predetermined frequency range that have to be covered by the audiogram generation method.

The audiogram generation can also be performed by an audiogram generation unit. The audiogram generation method can also be an algorithm or a mode of operation that can be executed on the control unit or the processing unit.

Preferably, the apparatus (in another embodiment, the hearing aid device) according to the disclosure is used to determine a cochlear dead region of a user. The first output sound and first subsequent output sound or n-th subsequent output sound are compared by a user, which decides, whether he hears a difference between the two sounds or not and gives a positive decision input or a negative decision input to the hearing aid device using the user interface. A negative decision input results in the detection of a cochlear dead region and a positive decision input leads to re-initialization of the comparison between two output sounds with adjusted parameters.

In an embodiment, the determined cochlear dead region is taken into account in order to provide sound information, such as speech information to the user. This may be implemented in the apparatus such as a hearing aid utilizing the technique known as frequency transposition. In principle, the term "frequency transposition" may imply a number of different approaches to altering the spectrum of a signal. For instance, "frequency compression" refers to compressing a (wider) source frequency region into a narrower target frequency region, e.g. by discarding every n-th frequency analysis band and "pushing" or "squeezing" the remaining bands together in the frequency domain. For example, if mid frequency residual hearing is available, then frequency compression may be applied on whole frequency range to make the whole frequency range audible. In context of the disclosure, "frequency shifting" refers to shifting at least a part of a first-frequency source region into a second-frequency target region without discarding or substantially retaining any spectral information contained in the shifted at least a part of the first-frequency band. Rather, the first frequencies that are transposed either replace the second frequencies completely or are mixed with the second frequencies. In principle, both types of approaches, "frequency compression" and "frequency shifting", can be performed on all or only some frequencies of a given input spectrum. In the context of this invention, both approaches are intended to transpose at least a part of the first frequencies to the second frequencies, either by compression or shifting. One such illustrative implementation wherein the higher frequencies are transposed to lower frequency is provided in EP2026601, which is incorporated here by reference. Other known techniques for frequency transposition may also be employed. Accordingly, the disclosure describes different frequency transposition schemes in dependent on the determined cochlear dead region.

In one embodiment, if the cochlear dead region is determined in a low frequency region, then the transposition on the received audio signal is made from the low frequency source region to the mid frequency target region. Additionally, in low frequency dead region scenario, a determination may be made whether the dead region is in speech range. If so, then the transposition is made else the transposition is made only in certain environments where it is dangerous for the user not to have audibility in the low frequency region.

In another embodiment, if the cochlear dead region is determined in a high frequency region, then the transposition on the received audio signal is made from the high frequency source region to mid frequency target region and/or to the low frequency target region.

In yet another embodiment, if the cochlear dead region is determined in a speech relevant mid frequency region (for example in cookie bite hearing loss), then the transposition on the received audio signal is made from the mid frequency source region to the low frequency target region and/or to the high frequency target region. Alternatively, the mid frequency source region comprises a first part of the received audio signal and a second part of the received audio signal, wherein the first part of the mid-frequency source region is transposed to the low frequency target region whereas the second part of the mid frequency source region is transposed to the high frequency target region.

In the embodiments disclosed in preceding paragraphs, the transposition is also dependent upon whether the frequency target region itself is a dead region or not. Therefore, residual hearing in the frequency region and/or feasibility of transposition may also be considered, thus determining where the sound will be made audible and what level. Accordingly, the disclosure offers a solution where the determined cochlear dead regions are avoided but are transposed to audible areas.

In an illustrative embodiment, the low frequency region is defined as below 250 Hz, mid frequency region is defined between 250 Hz to 4000 Hz, and the high frequency region is defined between above 4000 Hz. However, the skilled person would realise that other frequency ranges may also be used to define these low, mid and high frequency regions.

The disclosed frequency transposition schemes may be implemented in a fitting algorithm that may be configured to receive determined dead region information as an input from the in situ apparatus (discussed earlier) that is adapted to determine the dead regions. The fitting algorithm is configured to provide fitting settings to the apparatus such that the transposition schemes may be implemented into the apparatus.

The disclosure, thus describes the apparatus that is adapted to perform a frequency transposition of a set of received frequencies of an audio signal received by the apparatus, when worn by the user, during use of the apparatus to a transposed set of frequencies in dependent on the determined cochlear dead regions.

In one embodiment, the apparatus is a headphone, a telephone, a smartphone, a mobile phone, or other hearing or communication device.

DESCRIPTION OF THE ACCOMPANYING FIGURES

The disclosure will be more fully understood from the following detailed description of embodiments thereof, taken together with the drawings in which.

DETAILED DESCRIPTION

Figure 1:
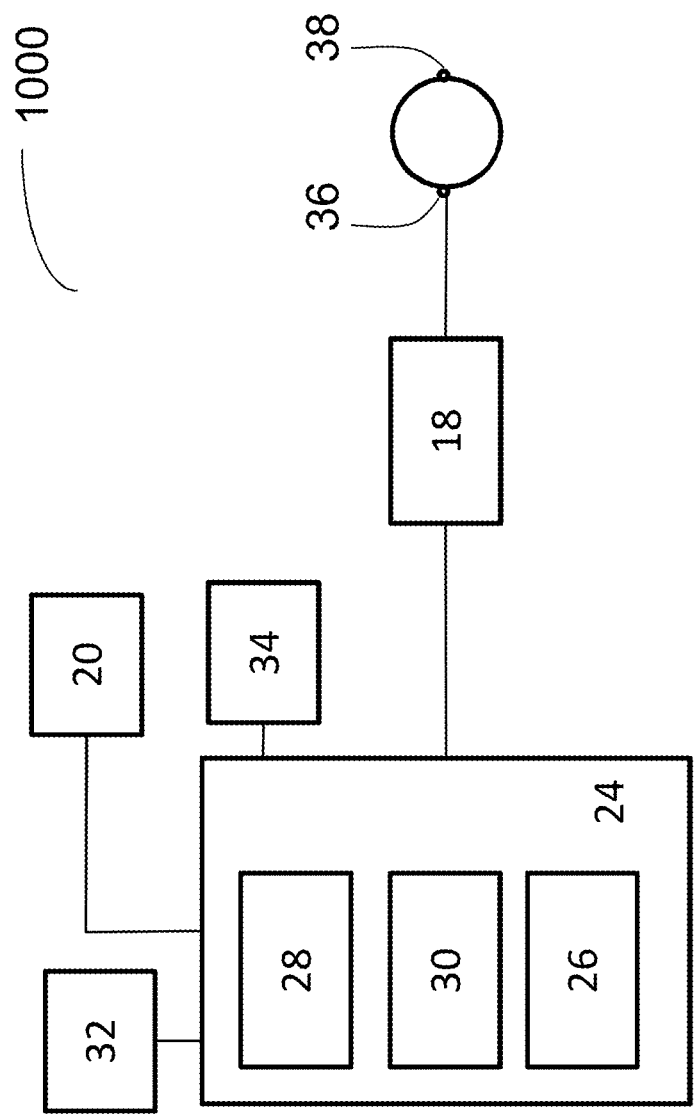
FIG. 1 shows a block diagram of the apparatus according to an embodiment of the disclosure.

FIG. 1 shows a block diagram of the apparatus according to an embodiment of the disclosure. The apparatus 1000 includes a control unit 24, a processing unit 26, a sound generation unit 28, a memory 30, a receiver unit 32, and a transmitter unit 34 and a user interface 20. In the present embodiment the processing unit 26, the sound generation unit 28 and the memory 30 are part of the control unit 24.

The sound generation unit (28) is configured to provide an electrical sound signal, and the output transducer (18) configured to generate an output sound corresponding to the electrical sound signal. The control unit (24) is configured to select a frequency region of interest and to cause the sound generation unit (28) to provide a first electrical sound signal representing a first predetermined frequency band adjacent to the frequency region of interest, with a first predetermined bandwidth, and a first predetermined sound pressure level. The control unit (24) is also configured to provide a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band. The first subsequent predetermined bandwidth is wider than the first predetermined bandwidth. The output transducer (18) is configured to generate a first output sound corresponding to the first electrical sound signal and a first subsequent output sound corresponding to the first subsequent electrical sound signal with the first subsequent predetermined time delay to the first electrical sound signal.

In this embodiment, each of the first predetermined sound pressure level and the n-th subsequent predetermined sound pressure level is equal to or above 80 dB SPL, such as equal to or above 80 dB SPL, such as equal to or above 90 dB SPL, such as equal to or above 100 dB SPL.

The sound generation unit (28) is configured to provide electrical sound signals that correspond to 1/f-pink noise with a predetermined frequency band, a predetermined frequency bandwidth, and a predetermined sound pressure level, and that generate an output sound with a predetermined duration when processed in an output transducer (18).

The apparatus (1000) also includes a user interface (20) configured to receive positive decision inputs and negative decision inputs by a user using the user interface (20) and to provide the positive decision inputs and negative decision inputs to the control unit (24). The control unit (24) is configured to provide an n-counter with n=1, and wherein the control unit (24) is configured to cause the sound generation unit (28), each time a positive decision input is received by the control unit (24) to increase the n-counter by 1, and to provide an n-th subsequent electrical sound signal representing an n-th subsequent predetermined frequency band comprising the frequency region of interest (86) with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth (96). The control unit (24) is configured, each time a positive decision input is received by the control unit (24), to cause the output transducer (18) to generate a first output sound corresponding to the first electrical sound signal and an n-th subsequent output sound corresponding to the n-th subsequent electrical sound signal with the n-th subsequent predetermined time delay to the first electrical sound signal. If a negative decision input is received by the control unit (24), the control unit (24) is configured to detect a cochlear dead region in the frequency band corresponding to the difference between the frequency bands of the first electrical sound signal and the n-th subsequent electrical sound signal.

The first output sound generated from the first electrical sound signal has a predetermined duration and a time delay between the first electrical sound signal and an n-th subsequent electrical sound signal has a duration corresponding to the predetermined duration. The predetermined duration of the first output sound may be equal to or below 5 s, such as equal to or below 2 s, such as equal to or below 1 s. The first predetermined bandwidth (90) of the first electrical sound signal is between 300 Hz and 2 kHz, such as between 500 Hz and 1500 Hz.

The memory (30) is configured to store audiogram data. In an audiogram generation mode, the control unit (24) is configured to cause the sound generation unit (28) to provide an electrical sound signal representing a predetermined frequency with a predetermined sound pressure level, the output transducer (18) is configured to generate an output sound corresponding to the electrical sound signal. The control unit (24) is further configured to increase the predetermined sound pressure level over time until a positive decision input for the predetermined frequency is received by the user interface (20) or a maximal threshold sound pressure level for the predetermined frequency is reached. The memory (30) is configured to store the sound pressure level for the predetermined frequency in audiogram data each time a positive decision input is received for a predetermined frequency or the maximal threshold sound pressure level for a predetermined frequency is reached. The control unit (24) is further configured to shift the predetermined frequency each time a positive decision input is received for a predetermined frequency or the maximal threshold sound pressure level for a predetermined frequency is reached. The control unit (24) is further configured to perform the audiogram mode for a predetermined frequency range and to generate an audiogram comprising user specific sound pressure levels in dependence of frequencies using the audiogram data.

The control unit (24) is configured to obtain an audiogram and to select a frequency region of interest in dependence of the audiogram. The control unit (24) may also be configured to identify a descent frequency region by determining a descent in the audiogram and to select the identified descent frequency region as frequency region of interest.

In an embodiment, the apparatus is a hearing aid device (FIGS. 1 & 2, 10, 10') configured to be worn on or at an ear (FIG. 3, 36, 38) of a user for in-situ determination of cochlear dead region. The apparatus, in this embodiment, is described in detail below in relation to the hearing aid device.

Figure 2:
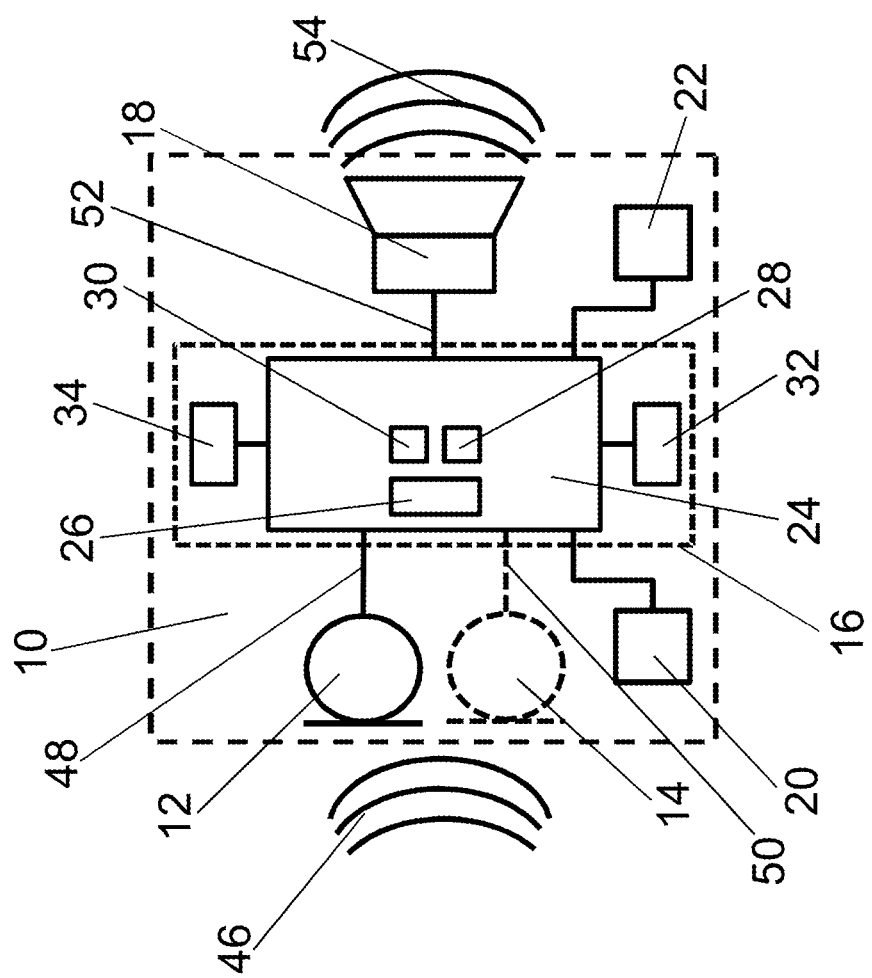
FIG. 2 shows a schematic illustration a hearing aid device according to an embodiment of the disclosure.

FIG. 2 shows an embodiment of a hearing aid device 10 with a microphone 12, a telecoil 14, electric circuitry 16, a speaker 18, a user interface 20 and a battery 22. In another embodiment the telecoil 14 can also be a second microphone, or a Bluetooth-Receiver, Infrared-Receiver, or any other wireless sound signal input configured to receive electrical sound signals wirelessly (not shown). In another embodiment the speaker 18 can also be a bone vibrator of a bone anchored hearing aid or an array of electrodes of a cochlear implant (not shown).

The electric circuitry 16 comprises a control unit 24, a processing unit 26, a sound generation unit 28, a memory 30, a receiver unit 32, and a transmitter unit 34. In the present embodiment the processing unit 26, the sound generation unit 28 and the memory 30 are part of the control unit 24. The hearing aid 10 is configured to be worn at an ear of a user. One hearing aid 10' can for example be arranged at a left ear 36 and one hearing aid 10 can be arranged at a right ear 38 of a user (see FIG. 3) with an insertion part 40 of the hearing aid 10 being arranged in an ear canal 42 of the user (as illustrated for the right ear 38).

The hearing aid 10 can be operated in various modes of operation, which are executed by the control unit 24 and use various components of the hearing aid 10. The control unit 24 is therefore configured to execute algorithms, to apply outputs on electrical signals processed by the control unit 24, and to perform calculations, e.g., for filtering, for amplification, for signal processing, or for other functions performed by the control unit 24 or its components. The calculations performed by the control unit 24 are performed on the processing unit 26. Executing the modes of operation includes the interaction of various components of the hearing aid 10, which are controlled by algorithms executed on the control unit 24.

In a hearing aid mode the hearing aid 10 is used as a hearing aid for hearing improvement by sound amplification and filtering. In an audiogram generation mode the hearing aid 10 is used to determine an audiogram 44 of a user (see FIG. 5). In a cochlear dead region determination mode the hearing aid 10 is used to determine a cochlear dead region of a user (see FIG. 5, FIG. 6, and FIG. 7).

The mode of operation of the hearing aid 10 can be manually selected by the user via the user interface 20 or automatically selected by the control unit 24, e.g., by receiving transmissions from an external device, obtaining an audiogram, receiving environment sound, receiving wireless sound signals or other indications that allow to determine that the user is in need of a specific mode of operation.

The hearing aid 10 operating in the hearing aid mode receives environment sound 46 with the microphone 12 and wireless sound signals with the telecoil 14. The microphone 12 generates electrical environment sound signals 48 and the telecoil 14 generates electrical wireless sound signals 50, which are provided to the control unit 24. If both electrical sound signals 48 and 50 are present in the control unit 24 at the same time, the control unit 24 can decide to process one or both of the electrical sound signals 48 and 50, e.g., as a linear combination. The processing unit 26 of the control unit 24 processes the electrical sound signals 48 and 50, e.g. by spectral filtering, frequency dependent amplifying, filtering, or other typical processing of electrical sound signals in a hearing aid generating an output sound signal 52. The processing of the electrical sound signals 48 and 50 by the processing unit 26 depends on various parameters, e.g., sound environment, sound source location, signal-to-noise ratio of incoming sound, cochlear dead region, mode of operation, type of output transducer, battery level, and/or other user specific parameters and/or environment specific parameters. The output sound signal 52 is provided to the speaker 18, which generates an output sound 54 corresponding to the output sound signal 52 which stimulates the hearing of the user.

Figure 4:
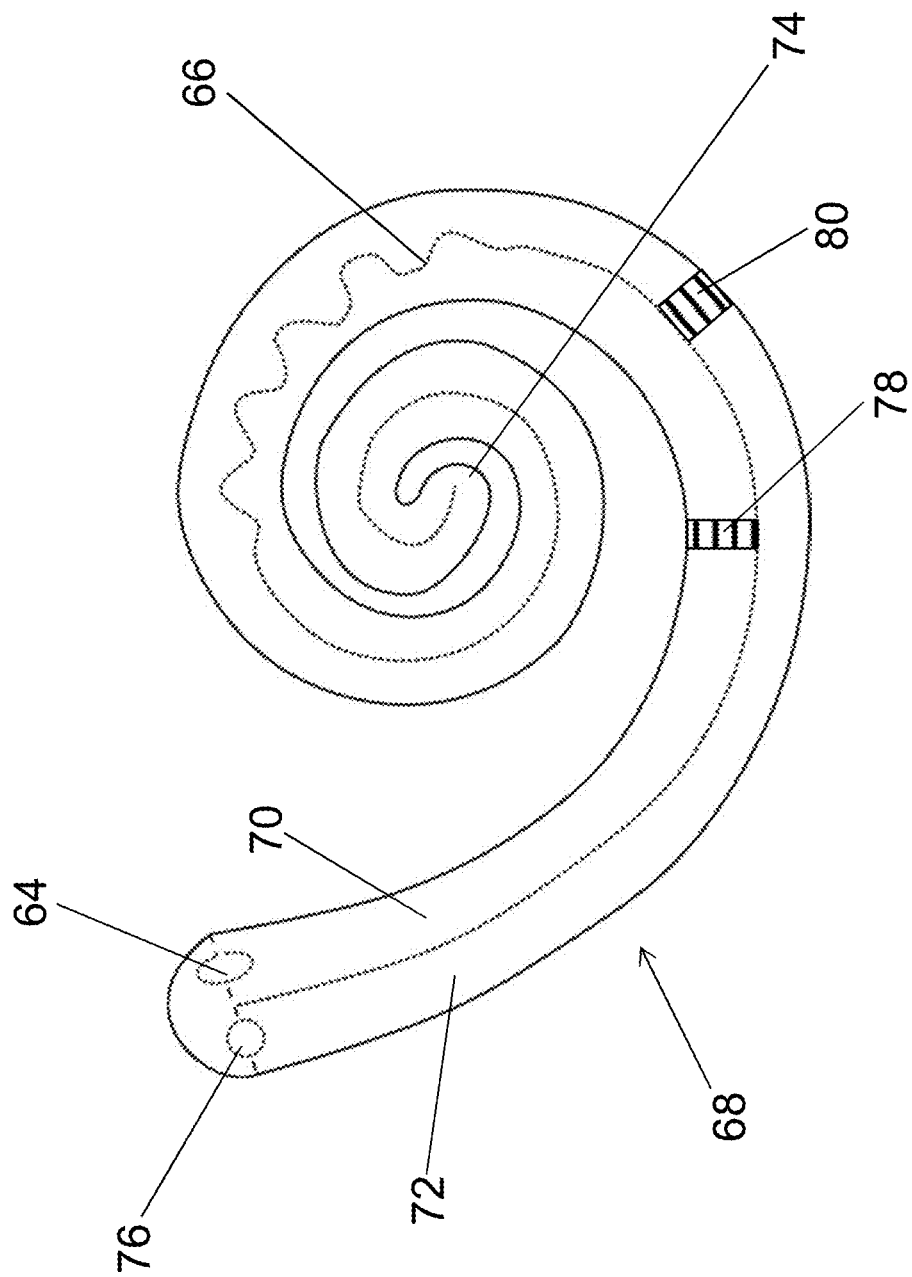
FIG. 4 shows a schematic illustration of an embodiment of a cochlea.

The audiogram generation mode of the hearing aid 10 is used to generate an audiogram 44 as presented in FIG. 4. User specific sound pressure levels representing a hearing threshold of a user are plotted in dependence of specific predetermined frequencies 82. The plotted frequency range is between 250 Hz and 8 kHz. The sound pressure level starts at 0 dB HL and the highest threshold detected for 8 kHz is at about 85 dB HL. A steep descent starts from 1 kHz with 20 dB HL to 2 kHz with 50 dB HL threshold. The steep descent is an indication for a frequency region of interest, where at least a part of the hair cells is expected to be dead or at least impaired.

When the hearing aid 10 is operated in the audiogram generation mode (see FIG. 5) the control unit 24 causes the sound generation unit 28 to provide an electrical sound signal representing a predetermined frequency with a predetermined sound pressure level. The sound generation unit 28 can generate the electrical sound signals or can retrieve them from another unit, e.g., the memory 30, the microphone 12, the telecoil 14, or the receiver unit 32. In this embodiment the sound generation unit 28 generates electrical sound signals representing a pure tone signal, i.e., a sine wave with a predetermined frequency and amplitude corresponding to the predetermined sound pressure level. The sound generation unit 28 provides the electrical sound signal to the speaker 18, which generates an output sound 54 corresponding to the electrical sound signal. A user listens to the output sound 54 and the user interface 20 waits for a response of the user to the output sound 54. The user interface 20 in this embodiment is a button to be manually operated by the user to give a decision input, but can also be any other interface that allows a decision input of a user to be received, e.g., electrodes connected to the skin or brain of the user, which record responses to the output sound 54. The decision input can for example be a positive decision or a negative decision, e.g., one of the decisions can be pushing the button and the other can be doing nothing for a predetermined duration or time limit, which will lead to the interpretation as a positive or negative decision.

The control unit 24 increases the predetermined sound pressure level of the electrical sound signal over time and causes the sound generation unit 28 to provide an electrical sound signal with an increased sound pressure level, until a positive decision input—representing the user's ability to hear the output sound 54—for the electrical sound signal representing the predetermined frequency is received by the user interface 20 or a maximal threshold sound pressure level for the electrical sound signal representing the predetermined frequency is reached. In this embodiment the sound pressure level is increased every 1 s, beginning with an initial sound pressure level of 0 dB SPL up to a sound pressure level of 100 dB SPL in steps of 10 dB. The sound pressure level can also be increased in other time intervals, such as in 5 s, 2 s or also below 1 s, e.g., 0.5 s. The step size of the sound pressure level increase can also be smaller than 10 dB, such as 5 dB, 2 dB, or 1 dB or higher than 10 dB, such as 20 dB. The sound pressure level step size and/or time interval step size can also be adaptive, meaning that each step can have an individual size. Instead of increasing the sound pressure level, the sound pressure level can also be decreased starting from e.g., 100 dB SPL down to 50 dB SPL.

When a positive decision input is received by the user interface 20 or the maximal threshold sound pressure level, in this embodiment 100 dB SPL, is reached, the current sound pressure level for the electrical sound signal representing the predetermined frequency is stored in the memory 30 together with the predetermined frequency as audiogram data.

The control unit 24 changes in response to receiving a positive decision input from the user interface 20 or in response to reaching the maximal threshold sound pressure level the value of the predetermined frequency. The control unit 24 in this embodiment selects a subsequent predetermined value for the predetermined frequency, resets the sound pressure level to 0 dB SPL, and causes the sound generation unit 28 to generate an electrical sound signal with the new parameters. The predetermined values for the predetermined frequency in this embodiment are 0.25 kHz, 0.5 kHz, 0.75 kHz, 1 kHz, 1.5 kHz, 2 kHz, 3 kHz, 4 kHz, 6 kHz and 8 kHz in a predetermined frequency range of 0.25 kHz to 8 kHz. The control unit 24 can shift the value of the predetermined frequency for example by increasing or decreasing the value of the predetermined frequency, e.g., with a fixed or adaptive step size, or by selecting random frequency values for the predetermined frequency or by randomly selecting predetermined values of the predetermined frequency, or other methods to shift the predetermined frequency known to the person skilled in the art. The step size can for example be smaller in a frequency region between 500 Hz and 4 kHz, accounting for the sensitivity of the human hearing, which is expected to be a region of interest showing a steep descent in hearing thresholds. The predetermined frequency range can also be between 10 Hz and 20 kHz, such as between 30 Hz and 12 kHz, such as between 200 Hz and 10 kHz covering the whole hearing spectrum of a human user.

The control unit 24 shifts the value of the predetermined frequency, until the predetermined frequency range is covered. The control unit 24 can also use other measures or inputs to determine when to stop generating new parameters for electrical sound signals, e.g., by a predetermined fixed number of different frequencies, by manual user input, or the like. When the predetermined frequency range is covered the control unit 24 generates an audiogram using the audiogram data, which is stored in the memory 30. The audiogram data can also form an audiogram without an intermediate step of generating an audiogram. The audiogram is a representation of user specific sound pressure level thresholds in dependence of frequency.

In an alternative audiogram generation mode the control unit 24 is configured to cause the sound generation unit 28 to provide an electrical sound signal representing a predetermined frequency with a predetermined sound pressure level, which is used by the speaker 18 to generate an output sound 54. The control unit 24 shifts the value of the predetermined frequency after a predetermined time duration or when a positive decision input is received and causes the sound generation unit 28 to provide an subsequent electrical sound signal, which is used by the output transducer to generate an output sound 54. The sound pressure level is unchanged until the whole frequency range is covered for a certain sound pressure level. When the whole frequency range is covered for a specific sound pressure level the control unit 24 shifts the value of the sound pressure level and causes the sound generation unit 28 to provide new electrical sound signals for the whole frequency range. The control unit 24 can also be configured to omit frequencies, for which a positive decision input has been previously received.

The cochlear dead region determination mode of the hearing aid 10 is used to determine a cochlear dead region 80 (see. FIG. 4). In FIG. 4 a schematic illustration of cochlea 68 is shown with a cochlear dead region 80. Sound waves enter the cochlea 68 via the oval window 64 in the perilymph filled vestibule (not shown), which allows to transmit the sound waves to the scala vestibuli 70 of the cochlea 68. The perilymph filled scala vestibuli 70 joins the perilymph filled scala tympani 72 at the apex 74 of the cochlea 68. The scala tympani 72 is connected to a round window 76, which vibrates with opposite phase to the oval window 64, e.g. the round window 76 moves out when a stirrup (not shown) pushes in the oval window 64 and allows movement of the liquid inside of the cochlea 68. The basilar membrane 66 determines the mechanical vibration propagation properties and is the base of the hair cells. The cochlea 68 serves for converting mechanical vibrations received by the ear drum 62 (see FIG. 3) into electrochemical nerve impulses which are then passed to the brain via the cochlear nerve.

Mechanical vibration stimuli transmitted by the perilymph run through the cochlea 68 and excite the basilar membrane 66 and the hair cells. Each frequency of the mechanical vibrations received has a specific place of resonance, i.e. frequency region 78 along the basilar membrane in the cochlea 68. A region of lower frequencies can be found in the scala vestibuli 70, increasing to higher frequencies in direction of the scala tympani 72. If hair cells in a region are dead, the region is classified as a cochlear dead region 80, as no auditory perception in this frequency range is possible. The regions of higher frequencies have a higher probability to be a cochlear dead region 80 and especially the sensitive frequency region between 2 kHz and 4 kHz for humans can contain impaired hair cells leading to a cochlear dead region 80 in this frequency range.

The cochlear dead region determination mode in the disclosure works as a comparison test instead of a threshold test like the threshold equalized noise (TEN) test. The user first generates an audiogram 44, e.g., in the conventional way known in the prior art or using the audiogram generation mode of the hearing aid 10. The audiogram 44 will in some cases be characteristic of the possibility of cochlear dead regions 80 for instance for steeply sloping audiograms 44 where the hearing gets worse with higher frequency. When this or other indications of the possibility of a cochlear dead region 80 are present, the user is subjected to a number of brief comparisons of narrow band output sounds, i.e., narrow band noise sounds, e.g., derived from 1/f pink noise. The inability to hear the difference between these narrow band output sounds serves to identify the presence and approximate nature of dead regions 80 in a cochlea 68 of one of the ears 36 or 38. Hence, the audiogram is used for guidance and supplementary knowledge is obtained through the use of narrow band output sound paired comparisons, i.e., the cochlear dead region determination mode of the hearing aid 10.

The frequency difference between the electrical sound signals in the narrow band output sound in any one pair of two narrow band output sounds is likely to be located within a cochlear dead region 80. If indeed this is the case, the user of the hearing aid 10 will not be able to tell the difference between the two output sounds. The choice of narrow band noise as narrow band output sound is preferred over pure tones, as the more frequency-narrow of the two electrical sound signals is wide enough in frequency to make it impossible for the output sound emitted in the cochlear dead region 80 to be sensed in neighbouring well functioning frequency regions of the cochlea 68 (at low frequencies in the example used), meaning that off-frequency listening is suppressed. Off-frequency listening, which is the phenomenon of sensing a sound at another frequency than where it is emitted is well established and one of the fundamental challenges related to cochlear dead region determination.

When the cochlear dead region determination mode is performed, it is relevant to use paired comparisons of a first electrical sound signal with a subsequent electrical sound signal, e.g., a second electrical sound signal, where the frequency content which varies within the pair of output sounds, i.e., difference 102 between the electrical sound signals (see FIG. 7) are guided by the audiogram 44. Hence, if the audiogram 44 indicates that a cochlear dead region 80 may exist from 3 kHz up, the control unit 24 is configured to select this region as a region of interest 86. If the cochlear dead region determination mode determines, that a cochlear dead region 80 is present in the frequency region of interest and the whole region is covered, then a cochlear dead region 80 is detected over the region of interest 86. If, however, a difference can be heard between the output sounds in the pair, the region is not dead. Part of the region may be dead and this may further be tested for by adjusting the frequencies, i.e., bandwidth in the electrical sound signals. On the basis of the audiogram data, a logical method can be developed optimizing the method to determine a cochlear dead region according to the above mentioned principles. In the following we provide one such embodiment of a cochlear dead region determination mode or method, which is to be understood as one of many possible ways to determine a cochlear dead region 80 using the above mentioned principles.

When the hearing aid 10 is operated in the cochlear dead region determination mode (see FIG. 5, FIG. 6, and FIG. 7) the control unit 24 at first obtains an audiogram 44. The audiogram 44 can be an audiogram 44 generated by the audiogram generation mode of the hearing aid 10, which is obtained from the memory 30. The control unit 24 can also obtain an audiogram 44 via the receiver unit 32 from an external device. The audiogram 44 shows user specific hearing level in dB HL representing a hearing threshold of the user plotted in dependence of specific predetermined frequencies 82 in Hz. The control unit 24 determines descents 84 in the audiogram 44 and selects a frequency region of interest 86 as a region comprising the descent 84.

A descent 84 can be understood as a change in hearing ability, i.e., higher sound pressure level threshold for a response to a pure tone at a specific frequency or in a specific frequency band or region.

Figure 6:
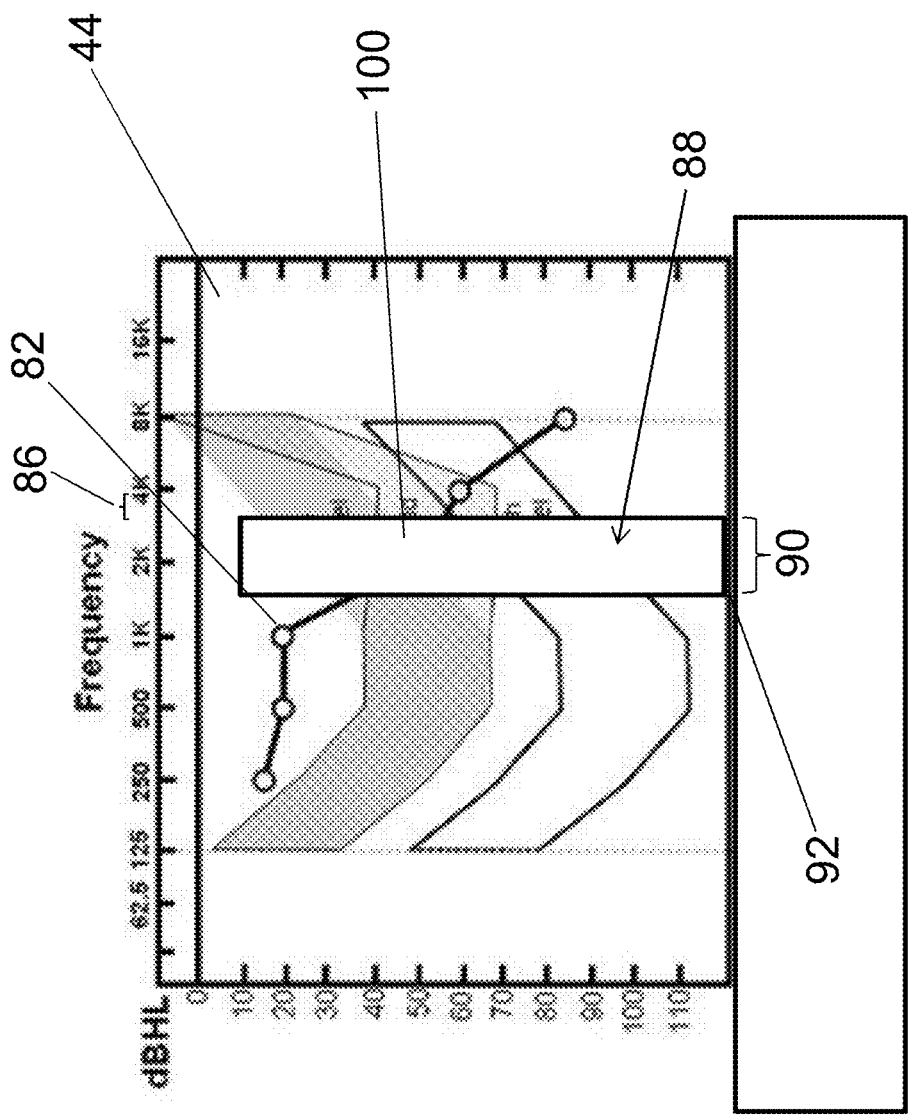
FIG. 6 shows a schematic audiogram of a user using the hearing aid device with a first narrow band masking sound.

The control unit 24 causes the sound generation unit 28 to provide a first electrical sound signal representing a first predetermined frequency band 88 adjacent to the frequency region of interest 86, with a first predetermined bandwidth 90, and a first predetermined sound pressure level 92 (see FIG. 6). In an embodiment, the first predetermined frequency band does not comprise a frequency of the frequency region of interest 86.

The first electrical sound signal is a narrow band noise emitted below the onset of the frequency region of interest 86, i.e., a possible cochlear dead region 80. The control unit 24 further causes the sound generation unit 28 to provide a second electrical sound signal representing a second predetermined frequency band 94 comprising the frequency region of interest 86 with a second predetermined bandwidth 96, a second predetermined sound pressure level 98, and a predetermined time delay to the first electrical sound signal (see FIG. 7). The second predetermined frequency band 94 comprises the first predetermined frequency band 88, and the second predetermined bandwidth 96 is wider than the first predetermined bandwidth 90 (see FIG. 7). The first predetermined bandwidth 90 is, however, wide enough in frequency to mask out any additional off-frequency listening components due to the part of the second electrical sound signal in the frequency region of interest 86, that has the wider second predetermined bandwidth 96. A part of the second predetermined bandwidth 96 is in the possible cochlear dead region. The speaker 18 is configured to generate a first output sound 100 corresponding to the first electrical sound signal and a second output sound 102 corresponding to the second electrical sound signal with the predetermined time delay to the first electrical sound signal. The predetermined time delay is here to be understood in a way, that the second output sound 102 is emitted as soon as the emission of the first output sound 100 stops.

The output sounds 100 and 102 are emitted to one of the ears 36 or 38 of the user for a predetermined duration. The predetermined duration can be controlled via the control unit 24. The control unit 24 can automatically select a predetermined duration in response to parameters obtained by the control unit 24 or it can be controlled manually by the user using the user interface 20 or by an external device connected to the hearing aid 10 via the receiver unit 32. The predetermined duration can be in a range of 0.5 s to 5 s. A default value for the predetermined duration of the output sounds 100 and 102 emitted to an ear is 1 s. The predetermined time delay can also be in a range of 0.5 s and 0.5 s and is in a default configuration adapted to the predetermined duration of the output sounds 100 and 102 in a way that the second output sound 102 is emitted without a time delay to the end of the first output sound 100. The emission of the output sounds 100 and 102 can also have individual predetermined durations, e.g., 0.5 s for the emission of output sound 100 and 1 s for the emission of output sound 102. The emission of the output sounds 100 and 102 can also be repeated, e.g., changing between emission of first output sound 100 and emission of second output sound 102. The user interface 20 and/or the control unit 24 can be configured to allow switching back and forth between the first output sound 100 and second output sound 102.

Further the values of the sound pressure levels of the first and second electrical sound signals can be equal or different. In the present embodiment the sound pressure levels have the same value, which is above an overall hearing threshold of the user. The output sounds in the present embodiment are narrow band noises created from filtering of for instance 1/f pink noise. The output sounds may also be any narrow band noise known to the person skilled in the art.

The output sounds 100 and 102 can also be emitted to both ears 36 and 38 at the same time. It is, however, preferable to emit the sounds 100 and 102 to one ear to determine a cochlear dead region 80 of one ear, e.g., the left ear 36, as the ears might have developed different cochlear dead regions 80.

The control unit is configured to provide an n-counter, which is an integer counter with n running from 0 to 20 in integer values in the present embodiment. The n-counter can also run to a higher integer value, e.g., 100, 500, or 1000 or a smaller integer value, e.g., 10, 5, or 3. The n-counter represents the number of different electrical sound signals provided by the sound generation unit 28 in the course of the cochlear dead region determination mode. The n-counter in the present embodiment is initialized with n=1, as two electrical sound signals have been provided by the sound generation unit 28. The n-counter can also count subsequent electrical sound signals running from 1 to 20 with the first electrical sound signal omitted by the counter, as the counter in this case only counts electrical sound signals subsequent to the first electrical sound signal.

After the emission of the output sounds 100 and 102 by the speaker 18 the control unit 24 in the present embodiment is configured to wait for a default time limit of 1 s for a decision input by the user interface 20. The time limit may also be configured for other time limit such as between 0.5 s and 5 s.

When the control unit 24 receives a positive decision, corresponding to a difference between the output sounds 100 and 102 as experienced by the user, the control unit increases the n-counter by 1. The control unit then provides a third electrical sound signal (or second subsequent sound signal with n=2) representing a third predetermined frequency band comprising the frequency region of interest 86 with a third predetermined bandwidth, a third predetermined sound pressure level, and a second predetermined time delay to the first electrical sound signal. The third predetermined frequency band comprises the first predetermined frequency band 88 and the third predetermined bandwidth is narrower than the second predetermined bandwidth 96. The bandwidth of the third electrical sound signal is reduced to reduce the cochlear region, corresponding to frequency region, which is stimulated by a third output sound generated from the third electrical sound signal, allowing to determine if also a fraction of the previous frequency region leads to a positive decision. The speaker 18 generates a first output sound 100 corresponding to the first electrical sound signal and a third output sound corresponding to the third electrical sound signal with the second subsequent predetermined time delay to the first electrical sound signal. The second predetermined time delay is in this embodiment identical to the predetermined time delay between the first electrical sound signal and the second electrical sound signal, but can also be different in another embodiment. Also the duration of the emission of the first output sound and third output sound are identical in this embodiment.

The control unit 24 again waits for a decision input and repeats to reduce the bandwidth of each subsequent electrical sound signal, e.g., fourth, fifth, . . . , twentieth electrical sound signal, until either a negative decision is received by the user interface 20 or the n-counter reaches a limit. The change of the bandwidth between a previous subsequent and a subsequent electrical sound signal, e.g., between the second and the third electrical sound signal, can be a constant fraction of the frequency region of interest, a current difference between the bandwidth of the first electrical sound signal and the current subsequent sound signal, an adaptive change of the bandwidth, or any suitable method to decrease or adapt the bandwidth of the subsequent electrical sound signal.

Figure 7:
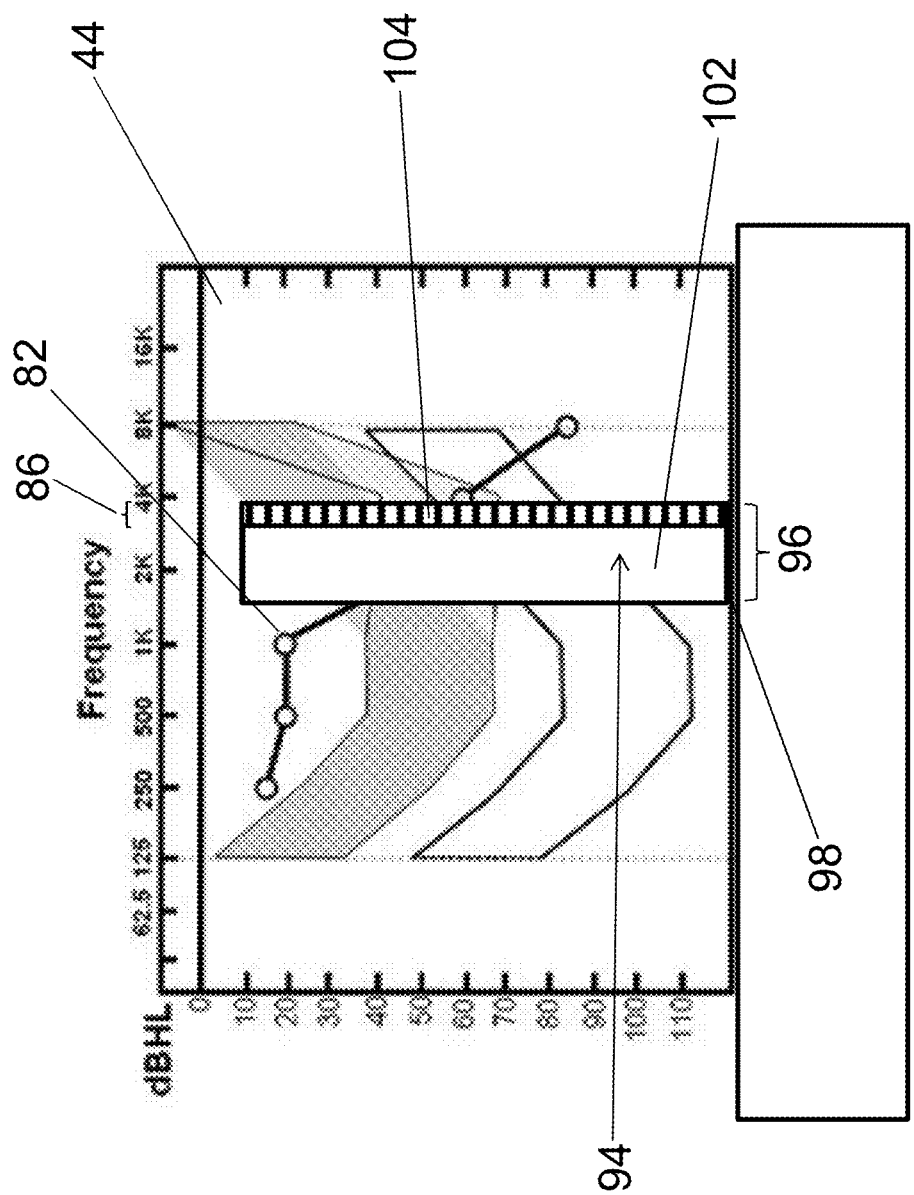
FIG. 7 shows a schematic audiogram of a user using the hearing aid device with a subsequent narrow band masking sound.

When a negative decision is received by the control unit 24, corresponding to a user not hearing any difference between the first output sound 100 and a subsequent output sound, e.g. the second output sound 102, the control unit 24 detects a cochlear dead region 80 in the frequency band corresponding to the difference 104 between the frequency band of the first electrical sound signal and the current subsequent electrical sound signal, e.g., the second sound signal in FIG. 7.

When no negative decision is received and the n-counter exceeds its limit no cochlear dead region 80 is detected and the frequency region of interest 86 does not contain a significant number of dead hair cells required to call the frequency region a cochlear dead region 80.

Figure 5:
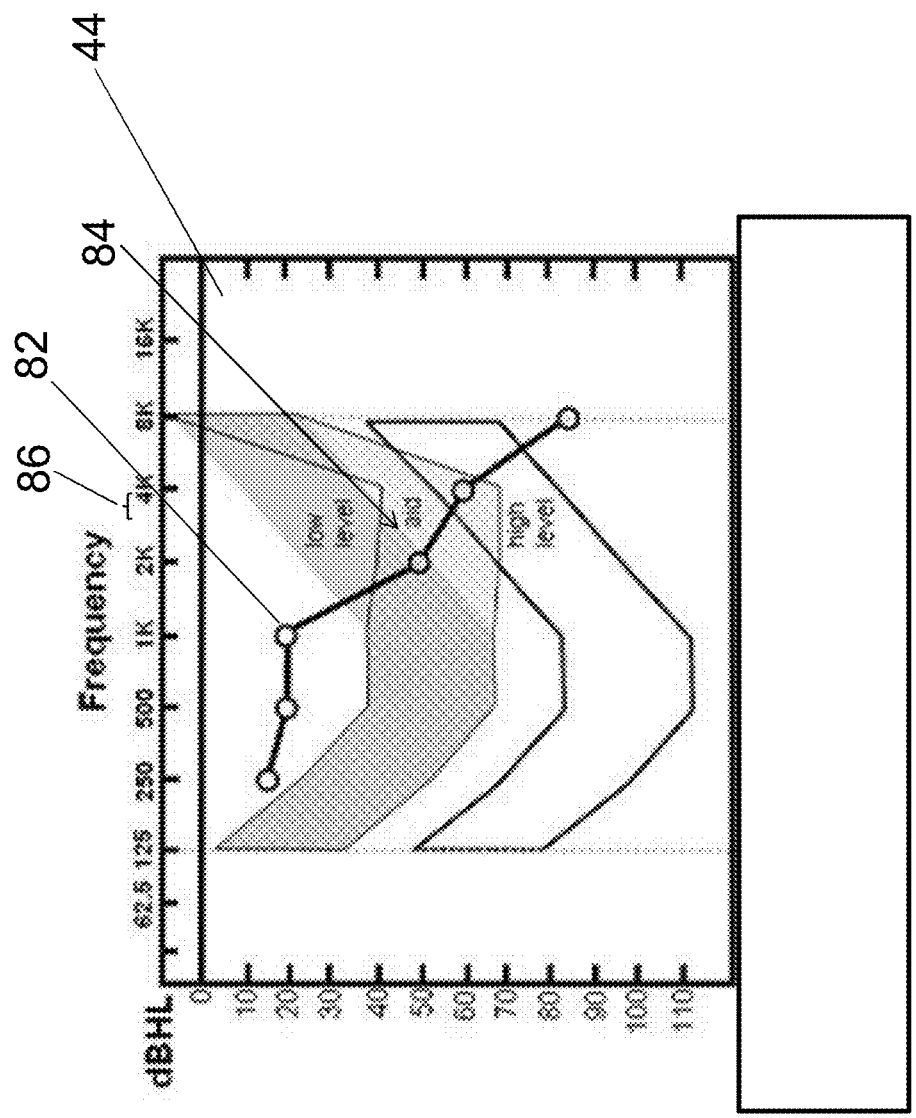
FIG. 5 shows a schematic audiogram of a user using the hearing aid device.

The cochlear dead region determination mode has been exemplified by high frequency hearing problems in FIG. 5, FIG. 6, and FIG. 7, which is the common case of a cochlear dead region 80. The cochlear dead region determination mode can also be extended to cochlear dead regions 80 at lower frequencies. For lower frequencies the first output sound generated from the first electrical sound signal is emitted at a frequency region above the region of interest 86, i.e., the region where a cochlear dead region 80 is assumed to be located.

The cochlear dead region determination mode of the hearing aid 10 allows in situ determination of the cochlear dead region 80, which is very useful. The same speaker 18 is used to perform the hearing aid mode, meaning amplification of hearing, and to perform the cochlear dead region determination. The user's individual ear acoustics are taken into account, no additional equipment is needed and there is no danger of collapsing canals that occur frequently when cochlear dead regions 80 are determined over headphones. In situ audiometry can be used to adapt hearing aid parameters to reduce over amplification in the high frequencies caused by phantom air bone gaps and higher thresholds that result due to collapsing canals.

The hearing aid 10 is powered by the battery 22 (see FIG. 2). The battery 22 has a low voltage between 1.35 V and 1.65 V. The voltage can also be in the range of 1 V to 5 V, such as between 1.2 V and 3 V.

The memory 30 is used to store data, e.g., pink 1/f noise, predetermined output sounds, predetermined electrical sound signals, predetermined time delays, audiograms, algorithms, operation mode instructions, or other data, e.g., used for the processing of electrical sound signals.

The receiver unit 32 and transmitter unit 34 allow the hearing aid 10 to connect to one or more external devices, e.g., a second hearing aid 10' (see FIG. 3), a mobile phone, an alarm, a personal computer or other devices. The receiver unit 32 and transmitter unit 34 receive and/or transmit, i.e., exchange, data with the external devices. The hearing aid 10 can for example exchange audiograms, pink 1/f noise, predetermined output sounds, predetermined electrical sound signals, predetermined time delays, audiograms, algorithms, operation mode instructions, software updates, or other data used, e.g., for operating the hearing aid 10. The receiver unit 32 and transmitter unit 34 can also be combined in a transceiver unit, e.g., a Bluetooth-transceiver, a wireless transceiver, or the like. The receiver unit 32 and transmitter unit 34 can also be connected with a connector for a wire, a connector for a cable or a connector for a similar line to connect an external device to the hearing aid 10.

Figure 3:
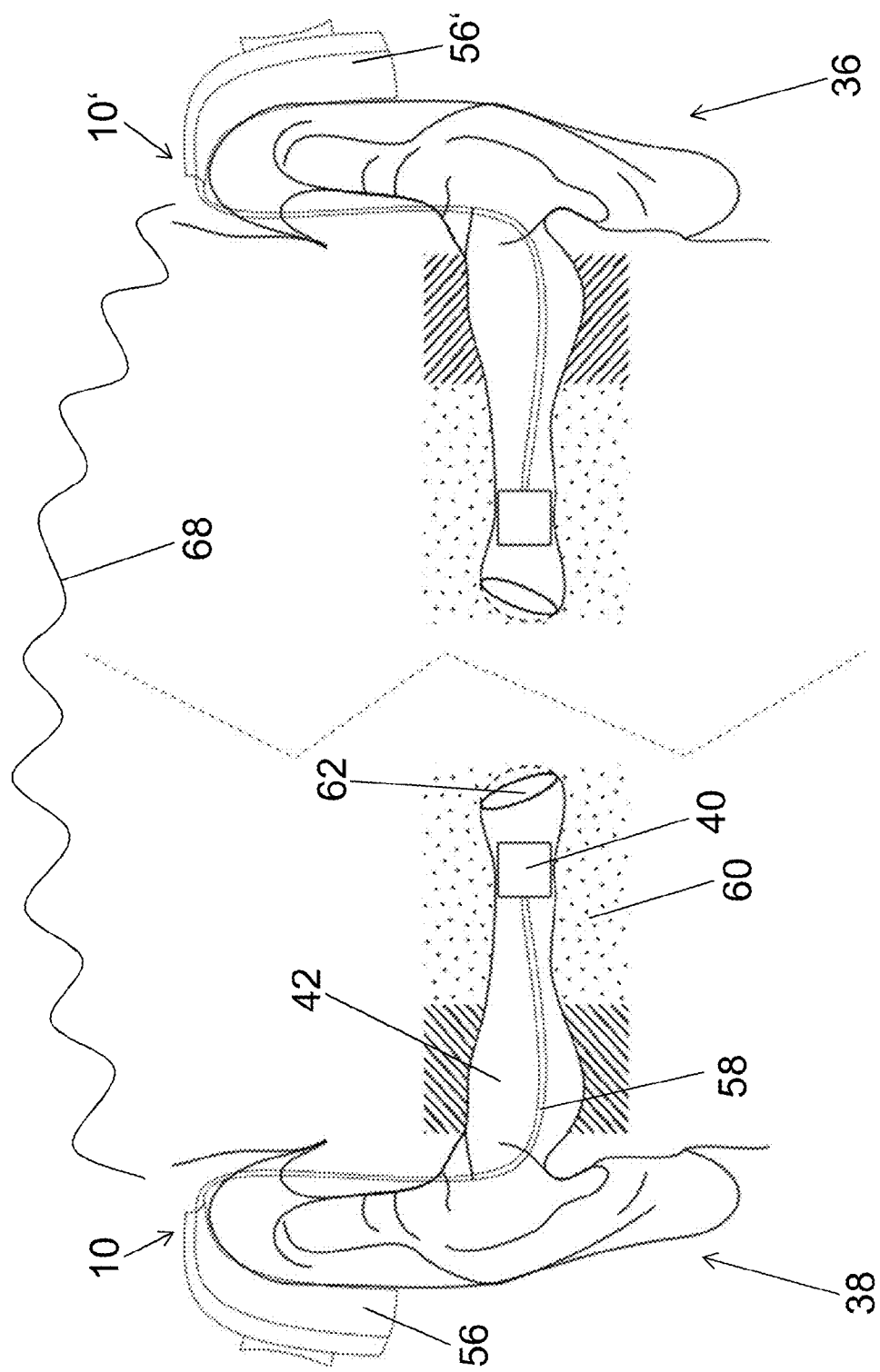
FIG. 3 shows a schematic illustration of an embodiment of a binaural hearing aid device worn at a left ear and at a right ear of a user.

FIG. 3 shows an embodiment of a binaural hearing aid comprising the hearing aids 10 and 10' each with a Behind-The-Ear (BTE) unit 56 and 56'. One BTE-unit 56 is mounted behind the right ear 38 and one BTE-unit 56' is mounted behind the left ear 36 of a user. Each of the BTE units comprises the microphone 12, the telecoil 14, the electric circuitry 16, the user interface 20, and the battery 22. The speaker 18 is arranged in the insertion part 40, which is connected to the BTE-unit 56 via the lead 58. The insertion part 40 is arranged in a bony portion 60 of the ear canal 42 of the user close to an ear drum 62. The insertion part 40 adheres to a skin portion of the bony portion 60 of the ear canal 42 to close and seal the ear canal 42, which prevents the escape and intrusion of sound. Output sound 54 generated by the speaker 18 stimulates the ear drum 62 which allows auditory perception via ossicles in the middle ear and, oval window 64, basilar membrane 66, hair cells and auditory nerves in the cochlea 68 of the inner ear (see FIG. 4).

Hearing aid 10 and hearing aid 10' each comprise a receiver unit 32 and a transmitter unit 34. The combination of receiver unit 32 and transmitter unit 34 can be used to connect the hearing aid 10 with other devices, e.g., with the hearing device 10' for binaural operation of the hearing aids 10 and 10'. If the hearing aids 10 and 10' are operated binaurally the two hearing aids 10 and 10' are connected with each other wirelessly. The transmitter unit 34 of the hearing aid 10 transmits data to the hearing aid 10' and the receiver unit 32 of the hearing aid 10 receives data from the hearing aid 10', and vice versa. The hearing aids 10 and 10' can exchange data, e.g., electrical sound signals 48 and 50, output sound signals 52, data signals, pink 1/f noise, audiograms, or other data, via the wireless connection 68.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An apparatus for determining cochlear dead region comprising
a sound generation unit configured to provide an electrical sound signal,
an output transducer configured to generate an output sound corresponding to the electrical sound signal, and
a control unit that determines a cochlear dead region,
wherein the control unit is configured to select a frequency region of interest and to cause the sound generation unit to provide
a first electrical sound signal representing a first predetermined frequency band adjacent to the frequency region of interest with a first predetermined bandwidth, and a first predetermined sound pressure level and
a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band and wherein the first subsequent predetermined bandwidth is wider than the first predetermined bandwidth and
wherein the output transducer is configured to generate
a first output sound corresponding to the first electrical sound signal and
a first subsequent output sound corresponding to the first subsequent electrical sound signal with the first subsequent predetermined time delay to the first electrical sound signal.

2. The apparatus according to claim 1, wherein the apparatus comprises a user interface configured to receive positive decision inputs and negative decision inputs by a user using the user interface and to provide the positive decision inputs and negative decision inputs to the control unit, wherein the control unit is configured to provide an n-counter with n=1, and
wherein the control unit is configured to cause the sound generation unit, each time a positive decision input is received by the control unit,
to increase the n-counter by 1, and
to provide an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth, and
wherein the control unit is configured, each time a positive decision input is received by the control unit, to cause the output transducer to generate
a first output sound corresponding to the first electrical sound signal and
an n-th subsequent output sound corresponding to the n-th subsequent electrical sound signal with the n-th subsequent predetermined time delay to the first electrical sound signal, and
wherein, if a negative decision input is received by the control unit, the control unit is configured to detect a cochlear dead region in the frequency band corresponding to the difference between the frequency bands of the first electrical sound signal and the n-th subsequent electrical sound signal.

3. The apparatus according to claim 2, wherein the apparatus comprises a memory configured to store audiogram data, and wherein, in an audiogram generation mode,
the control unit is configured to cause the sound generation unit to provide an electrical sound signal representing a predetermined frequency with a predetermined sound pressure level,
the output transducer is configured to generate an output sound corresponding to the electrical sound signal,
the control unit is further configured to increase the predetermined sound pressure level over time until a positive decision input for the predetermined frequency is received by the user interface or a maximal threshold sound pressure level for the predetermined frequency is reached,
the memory is configured to store the sound pressure level for the predetermined frequency in audiogram data each time a positive decision input is received for a predetermined frequency or the maximal threshold sound pressure level for a predetermined frequency is reached,
the control unit is further configured to shift the predetermined frequency each time a positive decision input is received for a predetermined frequency or the maximal threshold sound pressure level for a predetermined frequency is reached, and
the control unit is further configured to perform the audiogram mode for a predetermined frequency range and to generate an audiogram comprising user specific sound pressure levels in dependence of frequencies using the audiogram data.

4. The apparatus according to claim 1, wherein the control unit is configured to obtain an audiogram and to select a frequency region of interest in dependence of the audiogram.

5. The apparatus according to claim 1, wherein the control unit is configured to identify a descent frequency region by determining a descent in the audiogram and to select the identified descent frequency region as frequency region of interest.

6. The apparatus according to claim 1, wherein the apparatus is a hearing aid device configured to be worn on or at an ear of a user for in-situ determination of cochlear dead region.

7. The apparatus according to claim 1, wherein the first predetermined bandwidth of the first electrical sound signal is between 300 Hz and 2 kHz.

8. The apparatus according to claim 1, wherein the first output sound generated from the first electrical sound signal has a predetermined duration and a time delay between the first electrical sound signal and an n-th subsequent electrical sound signal has a duration corresponding to the predetermined duration.

9. The apparatus according to claim 8, wherein the predetermined duration of the first output sound is equal to or below 5 s.

10. The apparatus according to claim 1, wherein the sound generation unit is configured to provide electrical sound signals that correspond to 1/f-pink noise with a predetermined frequency band, a predetermined frequency bandwidth, and a predetermined sound pressure level, and that generate an output sound with a predetermined duration when processed in an output transducer.

11. The apparatus according to claim 1, wherein each of the first predetermined sound pressure level and an n-th subsequent predetermined sound pressure level is equal to or above 80 dB SPL.

12. The apparatus according to claim 1, wherein the apparatus is a hearing aid device, further comprising at least a microphone and electric circuitry, wherein the microphone is configured to receive environment sound and to generate electrical environment sound signals, wherein the electric circuitry is configured to process electrical environment sound signals and to generate output sound signals, and wherein the output transducer is configured to generate output sounds corresponding to the output sound signals.

13. The apparatus according to claim 1, wherein the apparatus is configured to perform a frequency transposition of a set of received frequencies of an audio signal received by the apparatus, when worn by the user, during use of the apparatus to a transposed set of frequencies in dependent on a determined cochlear dead region, wherein
   if the cochlear dead region is determined in a low frequency region, then the transposition on the received audio signal is made from the low frequency source region to the mid frequency target region; and/or
   if the cochlear dead region is determined in a speech relevant mid frequency region, then the transposition on the received audio signal is made from the mid frequency source region to the low frequency target region and/or to the high frequency target region or the mid frequency source region comprises a first part of the received audio signal and a second part of the received audio signal, wherein the first part of the mid-frequency source region is transposed to the low frequency target region whereas the second part of the mid frequency source region is transposed to the high frequency target region; and/or
   if the cochlear dead region is determined in a high frequency region, then the transposition on the received audio signal is made from the high frequency source region to mid frequency target region and/or to the low frequency target region.

14. The apparatus according to claim 1, wherein the apparatus is a headphone or a hearing aid device.

15. A method for determining cochlear dead regions of a user using an apparatus according to claim 1, comprising the steps:
   obtaining an audiogram,
   selecting a frequency region of interest in the audiogram,
   providing a first electrical sound signal representing a first predetermined frequency band adjacent to the frequency region of interest, with a first predetermined bandwidth and a first predetermined sound pressure level,
   providing a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band and wherein the first subsequent predetermined bandwidth is wider than the first predetermined bandwidth,
   emitting a first output sound corresponding to the first electrical sound signal for a first predetermined duration,
   emitting a first subsequent output sound corresponding to the first subsequent electrical sound signal with the first subsequent predetermined time delay to the first electrical sound signal for a first subsequent predetermined duration,
   providing an n-counter with n=1,
   receiving a positive decision input or a negative decision input in a predetermined time limit,
   each time a positive decision input is received within the predetermined time limit performing the steps
      increasing the n-counter by 1,
      providing an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth,
      emitting the first output sound corresponding to the first electrical sound signal for the first predetermined duration,
      emitting the n-th subsequent output sound corresponding to the n-th subsequent electrical sound signal with the n-th subsequent predetermined time delay to the first electrical sound signal for an n-th predetermined duration, and
      receiving a positive decision input or a negative decision input in a predetermined time limit,
   and
   detecting, if a negative decision input is received, a cochlear dead region in the frequency band corresponding to the difference between the frequency bands of the first electrical sound signal and the n-th subsequent electrical sound signal.

16. A method according to claim 15, wherein the method further performs the following initial steps for a predetermined frequency range to generate an audiogram
   providing an electrical sound signal representing a predetermined frequency with a predetermined sound pressure level,
   emitting an output sound corresponding to the electrical sound signal,
   increasing the predetermined sound pressure level over time until a positive decision input for the electrical sound signal representing the predetermined frequency is received or a maximal threshold sound pressure level for the electrical sound signal representing the predetermined frequency is reached,
   storing the sound pressure level for the predetermined frequency in audiogram data each time a positive decision input is received for a predetermined frequency or the maximal threshold sound pressure level for a predetermined frequency is reached, shifting the predetermined frequency each time a positive decision input is received for an electrical sound signal representing a predetermined frequency or the maximal threshold sound pressure level for an electrical sound signal representing a predetermined frequency is reached generating an audiogram comprising user specific sound pressure levels in dependence of frequencies using the audiogram data, if a predetermined number of audiogram data has been stored.

17. The method according to claim 15, further comprising performing a frequency transposition of a set of received frequencies of an audio signal received by the apparatus, when worn by the user, during use of the apparatus to a transposed set of frequencies in dependent on the determined cochlear dead regions, wherein if the cochlear dead region is determined in a low frequency region, then the transposition on the received audio signal is made from the low frequency source region to the mid frequency target region; and/or if the cochlear dead region is determined in a speech relevant mid frequency region, then the transposition on the received audio signal is made from the mid frequency source region to the low frequency target region and/or to the high frequency target region or the mid frequency source region comprises a first part of the received audio signal and a second part of the received audio signal, wherein the first part of the mid-frequency source region is transposed to the low frequency target region whereas the second part of the mid frequency source region is transposed to the high frequency target region; and/or if the cochlear dead region is determined in a high frequency region, then the transposition on the received audio signal is made from the high frequency source region to mid frequency target region and/or to the low frequency target region.

18. A method for determining cochlear dead regions of a user using an apparatus according to claim 2, comprising the steps:

obtaining an audiogram, selecting a frequency region of interest in the audiogram, providing a first electrical sound signal representing a first predetermined frequency band adjacent to the frequency region of interest, with a first predetermined bandwidth and a first predetermined sound pressure level, providing a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band and wherein the first subsequent predetermined bandwidth is wider than the first predetermined bandwidth, emitting a first output sound corresponding to the first electrical sound signal for a first predetermined duration, emitting a first subsequent output sound corresponding to the first subsequent electrical sound signal with the first subsequent predetermined time delay to the first electrical sound signal for a first subsequent predetermined duration, providing an n-counter with n=1, receiving a positive decision input or a negative decision input in a predetermined time limit, each time a positive decision input is received within the predetermined time limit performing the steps increasing the n-counter by 1, providing an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth, emitting the first output sound corresponding to the first electrical sound signal for the first predetermined duration, emitting the n-th subsequent output sound corresponding to the n-th subsequent electrical sound signal with the n-th subsequent predetermined time delay to the first electrical sound signal for an n-th predetermined duration, and receiving a positive decision input or a negative decision input in a predetermined time limit, and detecting, if a negative decision input is received, a cochlear dead region in the frequency band corresponding to the difference between the frequency bands of the first electrical sound signal and the n-th subsequent electrical sound signal.

19. A method for determining cochlear dead regions of a user using an apparatus according to claim 3, comprising the steps:

obtaining an audiogram, selecting a frequency region of interest in the audiogram, providing a first electrical sound signal representing a first predetermined frequency band adjacent to the frequency region of interest, with a first predetermined bandwidth and a first predetermined sound pressure level, providing a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band and wherein the first subsequent predetermined bandwidth is wider than the first predetermined bandwidth, emitting a first output sound corresponding to the first electrical sound signal for a first predetermined duration, emitting a first subsequent output sound corresponding to the first subsequent electrical sound signal with the first subsequent predetermined time delay to the first electrical sound signal for a first subsequent predetermined duration, providing an n-counter with n=1, receiving a positive decision input or a negative decision input in a predetermined time limit, each time a positive decision input is received within the predetermined time limit performing the steps increasing the n-counter by 1, providing an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth, emitting the first output sound corresponding to the first electrical sound signal for the first predetermined duration, emitting the n-th subsequent output sound corresponding to the n-th subsequent electrical sound signal with the n-th subsequent predetermined time delay to the first electrical sound signal for an n-th predetermined duration, and receiving a positive decision input or a negative decision input in a predetermined time limit, and detecting, if a negative decision input is received, a cochlear dead region in the frequency band corresponding to the difference between the frequency bands of the first electrical sound signal and the n-th subsequent electrical sound signal.

20. A method for determining cochlear dead regions of a user using an apparatus according to claim 4, comprising the steps:

obtaining an audiogram, selecting a frequency region of interest in the audiogram, providing a first electrical sound signal representing a first predetermined frequency band adjacent to the frequency region of interest, with a first predetermined bandwidth and a first predetermined sound pressure level, providing a first subsequent electrical sound signal representing a first subsequent predetermined frequency band comprising the frequency region of interest with a first subsequent predetermined bandwidth, a first subsequent predetermined sound pressure level, and a first subsequent predetermined time delay to the first electrical sound signal, wherein the first subsequent predetermined frequency band comprises the first predetermined frequency band and wherein the first subsequent predetermined bandwidth is wider than the first predetermined bandwidth, emitting a first output sound corresponding to the first electrical sound signal for a first predetermined duration, emitting a first subsequent output sound corresponding to the first subsequent electrical sound signal with the first subsequent predetermined time delay to the first electrical sound signal for a first subsequent predetermined duration, providing an n-counter with n=1, receiving a positive decision input or a negative decision input in a predetermined time limit, each time a positive decision input is received within the predetermined time limit performing the steps increasing the n-counter by 1, providing an n-th subsequent electrical sound signal representing an n-th subsequent predetermined frequency band comprising the frequency region of interest with an n-th subsequent predetermined bandwidth, an n-th subsequent predetermined sound pressure level, and an n-th subsequent predetermined time delay to the first electrical sound signal, wherein the n-th subsequent predetermined frequency band comprises the first predetermined frequency band and wherein the n-th subsequent predetermined bandwidth is narrower than the (n−1)-th subsequent predetermined bandwidth, emitting the first output sound corresponding to the first electrical sound signal for the first predetermined duration, emitting the n-th subsequent output sound corresponding to the n-th subsequent electrical sound signal with the n-th subsequent predetermined time delay to the first electrical sound signal for an n-th predetermined duration, and receiving a positive decision input or a negative decision input in a predetermined time limit, and detecting, if a negative decision input is received, a cochlear dead region in the frequency band corresponding to the difference between the frequency bands of the first electrical sound signal and the n-th subsequent electrical sound signal.

\* \* \* \* \*